United States Patent
Clough et al.

[11] Patent Number: 5,668,160
[45] Date of Patent: Sep. 16, 1997

[54] FUNGICIDAL OXAZOLYL AND OXADIAZOLYL DERIVATIVES

[75] Inventors: John Martin Clough, Marlow; Patrick Jelf Crowley, Crowthorne; John Stephen Delaney, Maidenhead, all of England

[73] Assignee: Zeneca Limited, London, England

[21] Appl. No.: 532,733

[22] PCT Filed: Mar. 15, 1994

[86] PCT No.: PCT/GB94/00502

§ 371 Date: Oct. 3, 1995

§ 102(e) Date: Oct. 3, 1995

[87] PCT Pub. No.: WO94/22844

PCT Pub. Date: Oct. 13, 1994

[30] Foreign Application Priority Data

Apr. 7, 1993 [GB] United Kingdom ............. 9307247

[51] Int. Cl.⁶ ............... C07D 271/06; A01N 43/76
[52] U.S. Cl. ............... 514/364; 514/374; 548/131; 548/143; 548/235
[58] Field of Search ............... 548/131, 143, 548/235; 514/364, 374

[56] References Cited

U.S. PATENT DOCUMENTS

| | | |
|---|---|---|
| 4,956,386 | 9/1990 | Wenderoth et al. . |
| 5,003,101 | 3/1991 | Brand et al. . |
| 5,086,064 | 2/1992 | Capiris ............... 514/365 |
| 5,254,717 | 10/1993 | Grammenos et al. . |
| 5,286,750 | 2/1994 | Mueller et al. . |
| 5,366,988 | 11/1994 | Toriyabe et al. . |

FOREIGN PATENT DOCUMENTS

| | | |
|---|---|---|
| 0 254 426 | 2/1988 | European Pat. Off. . |
| 0 331 061 | 9/1989 | European Pat. Off. . |
| 0 342 459 | 11/1989 | European Pat. Off. . |
| 0 398 692 | 11/1990 | European Pat. Off. . |
| 0 422 597 | 4/1991 | European Pat. Off. . |
| 0 499 823 | 8/1992 | European Pat. Off. . |
| 92/09581 | 6/1992 | WIPO . |

*Primary Examiner*—Robert Gerstl
*Attorney, Agent, or Firm*—Joseph R. Snyder; Marian T. Thomson

[57] ABSTRACT

A compound of formula (I) wherein Q is oxazol-2-yl, 1,3,4-oxadiazol-2-yl, $C_{1-4}$-oxadiazol-3-yl or 1,2,4-oxadiazol-5-yl; Z is CH or N; A is hydrogen, halogen, $C_{1-4}$ alkyl, 1,2,4 alkoxy, cyano, nitro or trifluoromethyl; X is halogen, optionally substituted alkyl, optionally substituted alkenyl, optionally substituted alkynyl, optionally substituted aryl, optionally substituted heteroaryl, optionally substituted cycloalkyl, $OR^1$, $SR^1$, $SOR^1$, $SO_2R^1$, $COR^1$, $CO_2R^1$, $NR^1R^2$ or $CONR^1R^2$; and $R^1$ and $R^2$ are, independently, hydrogen, optionally substituted alkyl, optionally substituted alkenyl, optionally substituted alkynyl, optionally substituted cycloalkyl, optionally substituted aryl or optionally substituted heteroaryl.

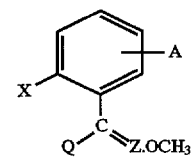

9 Claims, No Drawings

FUNGICIDAL OXAZOLYL AND OXADIAZOLYL DERIVATIVES

This application is a 371 of PCT/GB94/00502 filed Mar. 15, 1994.

The present invention relates to fungicidal oxazolyl and oxadiazolyl derivatives, to processes for preparing them, to fungicidal compositions comprising them and to methods of using them to combat fungi, especially fungal infections of plants.

Fungicidal alkoxyacrylate and oxyiminoacetate compounds are known. (See, for example, EP-A-178826, EP-A-242081, EP-A-253213, EP-A-370629, EP-A-382375 and WO 92/18487.) The present invention is distinguished from these known compounds by replacing the alkoxyacrylate or oxyiminoacetate group with the group Q—C=Z.OCH$_3$ (wherein Q and Z are as defined below).

According to the present invention there is provided a compound of formula (I), wherein Q is oxazol-2-yl, 1,3,4-oxadiazol-2-yl, 1,2,4-oxadiazol-3-yl or 1,2,4-oxadiazol-5-yl; Z is CH or N; A is hydrogen, halogen, C$_{1-4}$ alkyl, C$_{1-4}$ alkoxy, cyano, nitro or trifluoromethyl; X is halogen, optionally substituted alkyl, optionally substituted alkenyl, optionally substituted alkynyl, optionally substituted aryl, optionally substituted heteroaryl optionally substituted cycloalkyl OR$^1$, SR$^1$, SOR$^1$, SO$_2$R$^1$, COR$^1$, CO$_2$R$^1$, NR$^1$R$^2$ or CONR$^1$R$^2$; R$^1$ and R$^2$ and are, independently, hydrogen, optionally substituted alkyl, optionally substituted alkenyl, optionally substituted alkynyl, optionally substituted cycloalkyl, optionally substituted aryl or optionally substituted heteroaryl.

Optionally substituted alkyl includes alkyl substituted by one or more halogen atoms or by a hydroxy, alkoxy, haloalkoxy, aryl, aryloxy, heteroaryl, heteroaryloxy, cycloalkyl, arylthio or heteroarylthio group, or, when the optionally substituted alkyl group is a value of X, it can also be optionally substituted by an R$^{1'}$ R$^{2'}$C=NO group (wherein R$^{1'}$ and R$^{2'}$ independently, hydrogen, optionally substituted alkyl (for example, optionally substituted heterocyclylalkyl, optionally substituted cycloalkylalkyl, optionally substituted arylalkyl, optionally substituted heteroarylalkyl, optionally substituted heteroaryloxyalkyl or optionally substituted aryloxyalkyl), optionally substituted alkenyl, optionally substituted alkynyl, optionally substituted cycloalkyl, optionally substituted aryl, optionally substituted heteroaryl, optionally substituted alkoxy, optionally substituted aryloxy, optionally substituted heteroaryloxy, nitro, halogen, NR'R" (wherein R' and R" are as defined below) or cyano, or R$^{1'}$ and R$^{2'}$ join to form a carbocyclic or heterocyclic ring system (suitably a C$_{5-10}$ aliphatic, aromatic or mixed aliphatic/aromatic carbocyclic ring system, for example cyclopentyl, cyclohexyl or cyclohexadienonyl and such groups carrying a fused benzene ring and/or substituents such as methyl; or it may be a 5- to 10-membered heterocyclic ring system, for example tetrahydropyranyl)).

Optionally substituted alkenyl and optionally substituted alkynyl include alkenyl and alkynyl groups optionally substituted with halogen, aryl, aryloxy, arylthio, heteroaryl, heteroaryloxy or heteroarylthio.

Because the double bond of the Q—C=Z.OCH$_3$ group is unsymmetrically substituted, the compounds of the invention may be obtained in the form of mixtures of (E)- and (Z)-geometric isomers. However, these mixtures can be separated into individual isomers, and this invention embraces such isomers and mixtures thereof in all proportions including those which consist substantially of the (Z)-isomer and those which consist substantially of the (E)-isomer.

In one aspect the present invention provides a compound of formula (Ie), wherein A, Q and Z are as defined above; W is O, OCH$_2$, CH$_2$O, S, SCH$_2$, CH$_2$S, CH$_2$, CH$_2$CH$_2$, CH=CH, C≡C, R$^3$C=NOCH$_2$ (thus forming, with Y, the group YR$^3$C=NOCH$_2$ or NR$^4$; Y is optionally substituted aryl, optionally substituted heteroaryl, optionally substituted arylalkyl or heteroarylalkyl; R$^3$ is hydrogen, alkyl, cyano, NR$^4$R$^5$, haloalkyl or halogen; R$^4$ and R$^5$ are, independently, hydrogen, alkyl or arylalkyl.

Alkyl moieties and the alkyl moiety of alkoxy, haloalkyl, haloalkoxy, arylalkyl and heteroarylalkyl are straight or branched chain and preferably contain, unless otherwise stated, from 1 to 8, especially from 1 to 6 (for example 1 to 4) carbon atoms. Examples of alkyl moieties are methyl, ethyl, n-propyl, iso-propyl, n-butyl and tert-butyl.

Alkenyl and alkynyl groups are straight or branched chain and preferably contain from 2 to 8, especially from 2 to 6 (for example from 2 to 4) carbon atoms. Examples of these groups are vinyl, allyl, ethynyl and propargyl.

Cycloalkyl is suitably C$_{3-6}$ cycloalkyl, for example cyclopropyl and cyclohexyl, and cycloalkylalkyl is suitably C$_{3-6}$ cycloalkyl(C$_{1-4}$)alkyl, for example cyclopropylmethyl or cyclopropylethyl.

Halogen is typically fluorine, chlorine or bromine.

Aryl may be naphthyl but is preferably phenyl.

Heteroaryl, which is normally linked by one of its carbon atoms, includes 5- and 6-membered aromatic rings containing one or more heteroatoms selected from the list comprising oxygen, sulphur and nitrogen and can be fused to benzenoid ring systems. Examples of heteroaryl are pyridinyl, pyrimidinyl, pyridazinyl, pyrazinyl, 1,2,3-, 1,2,4- or 1,3,5-triazinyl, furyl, thienyl, pyrrolyl, pyrazolyl, imidazolyl, 1,2,3- or 1,2,4-triazolyl, oxazolyl, isoxazolyl, thiazolyl, isothiazolyl, quinolinyl, isoquinolinyl, cinnolinyl, quinazolinyl, quinoxalinyl, indolinyl, isoindolinyl, 1- or 2-benzofuranyl, 1- or 2-benzothienyl, benzimidazolinyl, 1,2,4-oxadiazolyl, 1,3,4-oxadiazolyl, 1,2,4-thiadiazolyl, 1,3,4-thiadiazolyl, benzisoxazolyl, benzisothiazolyl, benzpyrazolyl, benzoxazolyl, benzthiazolyl, tetrazolyl and thiazolo[5,4-b]pyrid-2-yl, and, where possible N-oxides thereof.

The foregoing aryl and heteroaryl rings may be optionally substituted with the following: halogen, hydroxy, mercapto, C$_{1-4}$ alkyl (especially methyl and ethyl), C$_{2-4}$ alkenyl (especially allyl), C$_{2-4}$ alkynyl (especially propargyl), C$_{1-4}$ alkoxy (especially methoxy), C$_{2-4}$ alkenyloxy (especially allyloxy), C$_{2-4}$ alkynyloxy (especially propargyloxy), halo(C$_{1-4}$)alkyl (especially trifluoromethyl), halo(C$_{1-4}$)alkoxy (especially trifluoromethoxy), C$_{1-4}$ alkylthio (especially methylthio), hydroxy(C$_{1-4}$)alkyl, C$_{1-4}$ alkoxy(C$_{1-4}$)alkyl, C$_{3-6}$ cycloalkyl, C$_{3-6}$ cycloalkyl(C$_{1-4}$) alkyl, optionally substituted methylenedioxy (especially optionally substituted with fluorine or C$_{1-4}$ alkyl), optionally substituted aryl (especially optionally substituted phenyl), optionally substituted heteroaryl (especially optionally substituted pyridyl or pyrimidinyl), optionally substituted heterocyclyl (especially optionally substituted pyrrolidine), optionally substituted aryloxy (especially optionally substituted phenoxy), optionally substituted heteroaryloxy (especially optionally substituted pyridyloxy or pyrimidinyloxy), optionally substituted aryl(C$_{1-4}$)alkyl (especially optionally substituted benzyl, optionally substituted phenethyl and optionally substituted phenyl n-propyl) in which the alkyl moiety is optionally substituted with hydroxy, optionally substituted heteroaryl(C$_{1-4}$)alkyl (especially optionally substituted pyridyl- or pyrimidinyl (C$_{1-4}$)alkyl), optionally substituted aryl(C$_{2-4}$)alkenyl (especially optionally substituted phenylethenyl) optionally substituted heteroaryl($C_{2-4}$)alkenyl (especially optionally substituted pyridylethenyl or pyrimidinylethenyl), optionally substituted aryl($C_{1-4}$)alkoxy (especially optionally substituted benzyloxy), optionally substituted heteroaryl($C_{1-4}$) alkoxy (especially optionally substituted pyridyl- or pyrimidinyl($C_{1-4}$)alkoxy), optionally substituted aryloxy ($C_{1-4}$)alkyl (especially phenoxymethyl), optionally substituted heteroaryloxy($C_{1-4}$)alkyl (especially optionally substituted pyridyloxy- or pyrimidinyloxy($C_{1-4}$)alkyl), acyloxy (including $C_{1-4}$ alkanoyloxy (especially acetyloxy) and benzoyloxy), cyano, thiocyanato, nitro, —NR'R", —NHCOR', —NHCONR'R", —CONR'R", —COOR', —OSO$_2$R', —SO$_2$R', —COR', —CR'=NR" or —N=CR'R" in which R' and R" are independently hydrogen, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy; when R' and R" are in CONR'R" they can together form a 5- or 6-membered heterocyclic ring (for example a pyrrolidine, piperidine or morpholine ring); or two substituents, when they are in adjacent positions on the aryl or heteroaryl ring can join to form a fused alphatic ring (especially to form a fused 6-membered carbon aliphatic ring).

Substituents which may be present in the aryl or heteroaryl rings of any of the foregoing substituents include one or more of the following: halo, hydroxy, mercapto, $C_{1-4}$ alkyl, $C_{2-4}$ alkenyl, $C_{1-4}$ alkynyl, $C_{1-4}$ alkoxy, $C_{2-4}$ alkenyloxy, $C_{2-4}$ alkynyloxy, halo($C_{1-4}$)alkyl, halo($C_{1-4}$) alkoxy, $C_{1-4}$ alkylthio, hydroxy($C_{1-4}$)alkyl, $C_{1-4}$ alkoxy($C_{1-4}$)alkyl, $C_{3-6}$ cycloalkyl, $C_{3-6}$ cycloalkyl($C_{1-4}$) alkyl, , alkanoyloxy, benzoyloxy, cyano, thiocyanato, nitro, —NR'R", —NHCOR', —NHCONR'R", —CONR'R", —COOR', —SO$_2$R', —OSO$_2$R', —COR', —CR'=NR" or —N=CR'R" in which R' and R" have the meanings given above.

In another aspect the present invention provides compounds wherein the alkoxyacrylate moiety of the compounds disclosed in EP-A-178826 is replaced by Q—C=Z.OCH$_3$, wherein Q and Z are as defined above. In a further aspect the present invention provides compounds wherein the alkoxyacrylate moiety of the compounds disclosed in EP-A-278595 is replaced by Q—C=Z.OCH$_3$, wherein Q and Z are as defined above. In a still further aspect the present invention provides a compound of formula (I) wherein A is hydrogen and X is optionally substituted aryloxymethyl or optionally substituted heteroaryloxymethyl, the aryl and heteroaryl rings preferably being substituted with one or more of the substituents outlined above.

In a further aspect the present invention provides compounds wherein the alkoxyacrylate moiety of the compounds disclosed in EP-A-242081 is replaced by Q—C=Z.OCH$_3$, wherein Q and Z are as defined above.

In a still further aspect the present invention provides compounds wherein the oxyiminoacetate moiety of the compounds disclose in EP-A-253213 is replaced by Q—C=Z.OCH$_3$, wherein Q and Z are as defined above.

In a further aspect the present invention provides compounds wherein the alkoxyacrylate moiety of the compounds disclosed in GB2193495-A is replaced by Q—C=Z.OCH$_3$, wherein Q and Z are as defined above. In a still further aspect the present invention provides a compound of formula (I) wherein A is hydrogen and X is optionally substituted heteroaryloxy, wherein the heteroaryl ring is a five membered C-linked ring containing one to four heteroatoms, which are the same or different and which are nitrogen, sulphur or oxygen and wherein adjacent substituents may together form a fused aromatic (such as benzene) or heteroaromatic (such as pyridine or pyrimidine) ring. It is preferred that the heteroaryl ring is optionally substituted by halogen, hydroxy, $C_{1-4}$ alkyl, $C_{1-4}$ alkoxy, halo($C_{1-4}$)alkyl (such as CF$_3$), halo($C_{1-4}$)alkoxy (such as OCF$_3$), nitro, NH$_2$, mono- or di-($C_{1-4}$)alkylamino, optionally substituted aryl, optionally substituted benzyl, optionally substituted heteroaryl or optionally substituted heteroarylmethyl.

In another aspect the present invention provides compounds wherein the alkoxyacrylate moiety of the compounds disclosed in EP-A-370629 is replaced by Q—C=Z.OCH$_3$, wherein Q and Z are as defined above. In a further aspect the present invention provides a compound of formula (I), wherein A is hydrogen; X is the group R$^1$R$^2$C=NOCH$_2$; R$^{1'}$ is optionally substituted phenyl, optionally substituted phenyl($C_{1-4}$)alkyl, optionally substituted phenoxy, optionally substituted phenoxy($C_{1-4}$)alkyl or optionally substituted heteroaryl (especially optionally substituted pyridyl, optionally substituted pyrimidinyl or optionally substituted quinolinyl); and R$^{2'}$ is hydrogen, $C_{1-4}$ alkyl (especially methyl) or cyano.

In yet another aspect the present invention provides compounds wherein the alkoxyacrylate moiety of the compounds disclosed in EP-A-382375 is replaced by Q—C=Z.OCH$_3$, wherein Q and Z are as defined above.

In a further aspect the present invention provides compounds wherein the alkoxyacrylate moiety of the compounds disclosed in WO 92/18487 is replaced by Q—C=Z.OCH$_3$, wherein Q and Z are as defined above.

In another aspect the present invention provides compounds of formula (I) wherein Z is CH or N; Q is oxazol-2-yl, 1,3,4-oxadiazol-2-yl or 1,2,4-oxadiazol-3-yl; A is hydrogen; X is phenoxy, $C_{1-4}$ alkyl (especially methyl), phenyloxymethyl (wherein the phenyl moiety is substituted by $C_{1-4}$ alkyl (especially methyl)) or R$^1$R$^{2'}$C=NOCH$_2$; R$^{1'}$ is $C_{1-4}$ alkyl (especially methyl); and R$^{2'}$ is phenyl substituted by $C_{1-4}$ haloalkyl (especially trifluoromethyl).

In a further aspect the present invention provides a compound of formula (I) wherein Z is CH or N; Q is oxazol-2-yl, 1,3,4-oxadiazol-2-yl, 1,2,4-oxadiazol-3-yl or 1,2,4-oxadiazol-5-yl; A is hydrogen; and X is $C_{1-4}$ alkyl, phenoxy (optionally substituted with halogen, $C_{1-4}$ alkyl, nitro, cyano, halo($C_{1-4}$)alkyl, benzyloxy, phenoxymethyl or phenoxy) 4-phenoxy-pyrimidin-6-yloxy (wherein the phenyl ring is optionally substituted by cyano, halogen, nitro, $C_{1-4}$ alkyl or $C_{1-4}$ alkoxy), phenoxymethyl (wherein the phenyl ring is optionally substituted by $C_{1-4}$ alkyl, halogen, cyano, nitro, halo($C_{1-4}$) alkyl, halo($C_{1-4}$)alkoxy phenyl, phenoxy, mono- or di-halophenoxy, benzyloxy or phenoxymethyl), pyridyloxymethyl (wherein the pyridyl ring is optionally substituted by halogen, $C_{1-4}$ alkyl, phenyl or halo($C_{1-4}$)alkyl), R$^{1'}$(CH$_3$) C=NOCH$_2$ (wherein R$^{1'}$ is a phenyl, pyridyl, quinolinyl, quinazolinyl, pyrazinyl or pyrimidinyl ring all of which are optionally substituted by halogen, cyano, nitro, $C_{1-4}$ alkyl, halo($C_{1-4}$)alkyl, phenyl, mono- or di-halophenyl, $C_{1-4}$ alkoxy, phenoxy or $C_{2-4}$ alkenyloxy) or phenyl-1,3,4-oxadiazolyloxy or phenyl-1,2,4-thiadiazolyloxy (wherein the phenyl rings are optionally substituted by halogen, $C_{1-4}$ alkyl, halo($C_{1-4}$)alkyl, nitro or cyano).

It is preferred that A is hydrogen.

In a still further aspect the present invention provides a compound of formula (I) wherein X is R$^1$R$^2$C=NOCH$_2$, R$^1$ is optionally substituted aryl, optionally substituted heteroaryl, optionally substituted aryloxy, optionally substituted heteroaryloxy, optionally substituted arylalkyloxy, optionally substituted heteroarylalkyloxy, optionally substituted aryloxyalkyl or optionally substituted heteroaryloxyalkyl; and $R^{2'}$ is methyl, cyano, hydrogen, chlorine or amino; and A, Z and Q are as defined above.

In another aspect the present invention provides a compound of formula (I) wherein X is optionally substituted aryloxymethyl, optionally substituted heteroaryloxymethyl or optionally substituted heteroaryloxy; and A, Z and Q are as defined above.

In yet another aspect the present invention provides a compound of formula (I) wherein Q is 1,3,4-oxadiazol-2-yl. When Q is 1,3,4-oxadiazol-2-yl it is preferred that Z is N.

In a further aspect the present invention provides a compound of formula (I) wherein Z is N or CH; Q is 1,3,4-oxadiazol-2-yl; A is hydrogen and X is as defined above.

The invention is illustrated by compounds of formula (I) which are listed in the following Tables. Unless stated otherwise, throughout these Tables the group $Q-C=Z.OCH_3$ has the (E)-configuration.

TABLE 1

Table 1 comprises 145 compounds of formula (If) wherein Z is CH and X has a value list.

| Compound No. | X |
|---|---|
| 1 | $CH_3$ |
| 2 | $C_6H_5O$ |
| 3 | 3-Cl—$C_6H_4O$ |
| 4 | 3-F—$C_6H_4O$ |
| 5 | 3-Br—$C_6H_4O$ |
| 6 | 3-$CH_3$—$C_6H_4O$ |
| 7 | 3-$NO_2$—$C_6H_4O$ |
| 8 | 3-CN—$C_6H_4O$ |
| 9 | 4-Cl—$C_6H_4O$ |
| 10 | 4-$CH_3$—$C_6H_4O$ |
| 11 | 4-CN—$C_6H_4O$ |
| 12 | 4-F—$C_6H_4O$ |
| 13 | 4-$CF_3$—$C_6H_4O$ |
| 14 | 3-$CF_3$—$C_6H_4O$ |
| 15 | 3,4-di-Cl—$C_6H_3O$ |
| 16 | 3-$C_6H_5O$—$C_6H_4O$ |
| 17 | 3-$C_6H_5OCH_2$—$C_6H_4O$ |
| 18 | 3-$C_6H_5CH_2O$—$C_6H_4O$ |
| 19 | 4-$C_6H_5O$—$C_6H_4O$ |
| 20 | 4-$C_6H_5O$-pyrimidin-6-yloxy |
| 21 | 4-(2-CN—$C_6H_4O$)-pyrimidin-6-yloxy |
| 22 | 4-(2-Cl—$C_6H_4O$)-pyrimidin-6-yloxy |
| 23 | 4-(2-$NO_2$—$C_6H_4O$)-pyrimidin-6-yloxy |
| 24 | 4-(2-$CH_3O$—$C_6H_4O$)-pyrimidin-6-yloxy |
| 25 | 4-(2-Br—$C_6H_4O$)-pyrimidin-6-yloxy |
| 26 | 4-(2-$CH_3$—$C_6H_4O$)-pyrimidin-6-yloxy |
| 27 | 4-(2-$C_2H_5$—$C_6H_4O$)-pyrimidin-6-yloxy |
| 28 | 4-(2-$CF_3$—$C_6H_4O$)-pyrimidin-6-yloxy |
| 29 | 4-(2-$C_2H_5O$—$C_6H_4O$)-pyrimidin-6-yloxy |
| 30 | 4-(2,6-di-F—$C_6H_3O$)-pyrimidin-6-yloxy |
| 31 | 4-(2-n-$C_3H_7O$—$C_6H_4O$)-pyrimidin-6-yloxy |
| 32 | 4-(2-n-$C_4H_9O$—$C_6H_4O$)-pyrimidin-6-yloxy |
| 33 | 4-(2-F—$C_6H_4O$)-pyrimidin-6-yloxy |
| 34 | $C_6H_5OCH_2$ |
| 35 | 2-$CH_3$—$C_6H_4OCH_2$ |
| 36 | 2-Cl—$C_6H_4OCH_2$ |
| 37 | 2-F—$C_6H_4OCH_2$ |
| 38 | 2-Br—$C_6H_4OCH_2$ |
| 39 | 2-$C_2H_5$—$C_6H_4OCH_2$ |
| 40 | 3-$CH_3$—$C_6H_4OCH_2$ |
| 41 | 3-Cl—$C_6H_4OCH_2$ |
| 42 | 3-F—$C_6H_4OCH_2$ |
| 43 | 3-CN—$C_6H_4OCH_2$ |
| 44 | 3-$CF_3$—$C_6H_4OCH_2$ |
| 45 | 3-$NO_2$—$C_6H_4OCH_2$ |
| 46 | 3-Br—$C_6H_4OCH_2$ |
| 47 | 3-$CF_3O$—$C_6H_4OCH_2$ |
| 48 | 3-$CH_3O$—$C_6H_4OCH_2$ |
| 49 | 3-$C_6H_5$—$C_6H_4OCH_2$ |
| 50 | 3-$C_6H_5O$—$C_6H_4OCH_2$ |
| 51 | 3-(3-F—$C_6H_4O$)—$C_6H_4OCH_2$ |
| 52 | 3-(3-Cl—$C_6H_4O$)—$C_6H_4OCH_2$ |
| 53 | 3-$C_6H_5CH_2O$—$C_6H_4OCH_2$ |
| 54 | 3-$C_6H_5OCH_2$—$C_6H_4OCH_2$ |
| 55 | 4-$CH_3$—$C_6H_4OCH_2$ |
| 56 | 4-Cl—$C_6H_4OCH_2$ |
| 57 | 4-F—$C_6H_4OCH_2$ |
| 58 | 4-CN—$C_6H_4OCH_2$ |
| 59 | 4-$C_6H_5$—$C_6H_4OCH_2$ |
| 60 | (E)-$C_6H_5C(CH_3)$=$NOCH_2$ |
| 61 | (E)-3-Cl—$C_6H_4C(CH_3)$=$NOCH_2$ |
| 62 | (E)-3-$CF_3$—$C_6H_4C(CH_3)$=$NOCH_2$ |
| 63 | (E)-3-$CH_3$—$C_6H_4C(CH_3)$=$NOCH_2$ |
| 64 | (E)-3-F—$C_6H_4C(CH_3)$=$NOCH_2$ |
| 65 | (E)-3-Br—$C_6H_4C(CH_3)$=$NOCH_2$ |
| 66 | (E)-3-CN—$C_6H_4C(CH_3)$=$NOCH_2$ |
| 67 | (E)-3-$NO_2$—$C_6H_4C(CH_3)$=$NOCH_2$ |
| 68 | (E)-3-$CH_3O$—$C_6H_4C(CH_3)$=$NOCH_2$ |
| 69 | (E)-4-Cl—$C_6H_4C(CH_3)$=$NOCH_2$ |
| 70 | (E)-4-F—$C_6H_4C(CH_3)$=$NOCH_2$ |
| 71 | (E)-4-$CH_3$—$C_6H_4C(CH_3)$=$NOCH_2$ |
| 72 | (E)-4-$CF_3$—$C_6H_4C(CH_3)$=$NOCH_2$ |
| 73 | (E)-4-CN—$C_6H_4C(CH_3)$=$NOCH_2$ |
| 74 | (E)-3-$C_6H_5$—$C_6H_4C(CH_3)$=$NOCH_2$ |
| 75 | (E)-3-(3-F—$C_6H_4$)—$C_6H_4C(CH_3)$=$NOCH_2$ |
| 76 | (E)-3-(3-Cl—$C_6H_4$)—$C_6H_4C(CH_3)$=$NOCH_2$ |
| 77 | (E)-3-$C_6H_5O$—$C_6H_4C(CH_3)$=$NOCH_2$ |
| 78 | (E)-3-(3-F—$C_6H_4$)—$C_6H_4C(CH_3)$=$NOCH_2$ |
| 79 | (E)-3-(3-Cl—$C_6H_4$)—$C_6H_4C(CH_3)$=$NOCH_2$ |
| 80 | (E)-4-$C_6H_5$—$C_6H_4C(CH_3)$=$NOCH_2$ |
| 81 | (E)-4-$C_6H_5O$—$C_6H_4C(CH_3)$=$NOCH_2$ |
| 82 | pyrid-2-yl$OCH_2$ |
| 83 | 5-Cl-pyrid-2-yl$OCH_2$ |
| 84 | 5-Br-pyrid-2-yl$OCH_2$ |
| 85 | 5-F-pyrid-2-yl$OCH_2$ |
| 86 | 5-$CH_3$-pyrid-2-yl$OCH_2$ |
| 87 | 5-$CF_3$-pyrid-2-yl$OCH_2$ |
| 88 | 6-Cl-pyrid-2-yl$OCH_2$ |
| 89 | 6-Br-pyrid-2-yl$OCH_2$ |
| 90 | 6-F-pyrid-2-yl$OCH_2$ |
| 91 | 6-$CH_3$-pyrid-2-yl$OCH_2$ |
| 92 | 6-$CF_3$-pyrid-2-yl$OCH_2$ |
| 93 | 5-$C_6H_5$-pyrid-2-yl$OCH_2$ |
| 94 | 6-$C_6H_5$-pyrid-2-yl$OCH_2$ |
| 95 | quinolin-2-yl$OCH_2$ |
| 96 | (E)-(pyrid-2-yl)C($CH_3$)=$NOCH_2$ |
| 97 | (E)-(4-$CF_3$-pyrid-2-yl)C($CH_3$)=$NOCH_2$ |
| 98 | (E)-(4-$C_2H_5O$-pyrimidin-2-yl)C($CH_3$)=$NOCH_2$ |
| 99 | (E)-(4-iso-$C_3H_7O$-pyrimidin-2-yl)C($CH_3$)=$NOCH_2$ |
| 100 | (E)-(4-$CF_3CH_2O$-pyrimidin-2-yl)C($CH_3$)=$NOCH_2$ |
| 101 | (E)-(4-tert-$C_4H_9O$-pyrimidin-2-yl)C($CH_3$)=$NOCH_2$ |
| 102 | (E)-(4-$CH_3$-pyrimidin-2-yl)C($CH_3$)=$NOCH_2$ |
| 103 | (E)-(4-tert-$C_4H_9$-pyrimidin-2-yl)C($CH_3$)=$NOCH_2$ |
| 104 | (E)-(4-$CF_3$-pyrimidin-2-yl)C($CH_3$)=$NOCH_2$ |
| 105 | (E)-(4-$C_2F_5$-pyrimidin-2-yl)C($CH_3$)=$NOCH_2$ |
| 106 | (E)-(4,5-di-$CH_3$-pyrimidin-2-yl)C($CH_3$)=$NOCH_2$ |
| 107 | (E)-(4-iso-$C_3H_7O$-5-$CH_3$-pyrimidin-2-yl)C($CH_3$)=$NOCH_2$ |
| 108 | (E)-(4-iso-$C_3H_7O$-5-F-pyrimidin-2-yl)C($CH_3$)=$NOCH_2$ |
| 109 | (E)-(4-$CF_3CH_2O$-5-F-pyrimidin-2-yl)C($CH_3$)=$NOCH_2$ |
| 110 | (E)-(4-n-$C_3H_7$-pyrimidin-2-yl)C($CH_3$)=$NOCH_2$ |
| 111 | (E)-(6-$C_2H_5O$-pyrimidin-4-yl)C($CH_3$)=$NOCH_2$ |
| 112 | (E)-(6-iso-$C_3H_7O$-pyrimidin-4-yl)C($CH_3$)=$NOCH_2$ |
| 113 | (E)-(6-$CF_3CH_2O$-pyrimidin-4-yl)C($CH_3$)=$NOCH_2$ |
| 114 | (E)-(6-allylO-pyrimidin-4-yl)C($CH_3$)=$NOCH_2$ |
| 115 | (E)-(quinolin-2-yl)C($CH_3$)=$NOCH_2$ |
| 116 | (E)-(quinolin-4-yl)C($CH_3$)=$NOCH_2$ |
| 117 | (E)-(quinazolin-4-yl)C($CH_3$)=$NOCH_2$ |
| 118 | (E)-(pyrazin-2-yl)C($CH_3$)=$NOCH_2$ |
| 119 | 5-($C_6H_5$)-(1,3,4-oxadiazol-2-yl)O |
| 120 | 5-(3-Cl—$C_6H_4$)-(1,3,4-oxadiazol-2-yl)O |
| 121 | 5-(3-F—$C_6H_4$)-(1,3,4-oxadiazol-2-yl)O |
| 122 | 5-(3-$CF_3$—$C_6H_4$)-(1,3,4-oxadiazol-2-yl)O |

-continued

| Compound No. | X |
|---|---|
| 123 | 5-(3-NO$_2$—C$_6$H$_4$)-(1,3,4-oxadiazol-2-yl)O |
| 124 | 5-(3-CN—C$_6$H$_4$)-(1,3,4-oxadiazol-2-yl)O |
| 125 | 5-(4-Cl—C$_6$H$_4$)-(1,3,4-oxadiazol-2-yl)O |
| 126 | 5-(4-F—C$_6$H$_4$)-(1,3,4-oxadiazol-2-yl)O |
| 127 | 5-(4-CF$_3$—C$_6$H$_4$)-(1,3,4-oxadiazol-2-yl)O |
| 128 | 5-(4-NO$_2$—C$_6$H$_4$)-(1,3,4-oxadiazol-2-yl)O |
| 129 | 5-(3-CH$_3$—C$_6$H$_4$)-(1,3,4-oxadiazol-2-yl)O |
| 130 | 5-(4-CH$_3$—C$_6$H$_4$)-(1,3,4-oxadiazol-2-yl)O |
| 131 | 5-(4-CN—C$_6$H$_4$)-(1,3,4-oxadiazol-2-yl)O |
| 132 | 3-(C$_6$H$_5$)-(1,2,4-thiadiazol-5-yl)O |
| 133 | 3-(3-Cl—C$_6$H$_4$)-(1,2,4-thiadiazol-5-yl)O |
| 134 | 3-(3-F—C$_6$H$_4$)-(1,2,4-thiadiazol-5-yl)O |
| 135 | 3-(3-CF$_3$—C$_6$H$_4$)-(1,2,4-thiadiazol-5-yl)O |
| 136 | 3-(3-NO$_2$—C$_6$H$_4$)-(1,2,4-thiadiazol-5-yl)O |
| 137 | 3-(3-CN—C$_6$H$_4$)-(1,2,4-thiadiazol-5-yl)O |
| 138 | 3-(3-CH$_3$—C$_6$H$_4$)-(1,2,4-thiadiazol-5-yl)O |
| 139 | 3-(4-Cl—C$_6$H$_4$)-(1,2,4-thiadiazol-5-yl)O |
| 140 | 3-(4-F—C$_6$H$_4$)-(1,2,4-thiadiazol-5-yl)O |
| 141 | 3-(4-CF$_3$—C$_6$H$_4$)-(1,2,4-thiadiazol-5-yl)O |
| 142 | 3-(4-NO$_2$—C$_6$H$_4$)-(1,2,4-thiadiazol-5-yl)O |
| 143 | 3-(4-CN—C$_6$H$_4$)-(1,2,4-thiadiazol-5-yl)O |
| 144 | 3-(4-CH$_3$—C$_6$H$_4$)-1,2,4-thiadiazol-5-yl)O |
| 145 | 2-CN—C$_6$H$_4$OCH$_2$ |

TABLE 2

Table 2 comprises 145 compounds of formula (If), wherein Z is N and X has the value listed for the corresponding numbered compound in Table 1.

TABLE 3

Table 3 comprises 145 compounds of formula (Ig), wherein Z is CH and X has the value listed for the corresponding numbered compounds in Table 1.

TABLE 4

Table 4 comprises 145 compounds of formula (Ig), wherein Z is N and X has the value listed for the correspondingly numbered compound in Table 1.

TABLE 5

Table 5 comprises 145 compounds of formula (Ih) wherein Z is CH and X has the value listed for the correspondingly numbered compound in Table 1.

TABLE 6

Table 6 comprises 145 compounds of formula (Ih) wherein Z is N and X has the value listed for the corresponding numbered compound in Table 1.

TABLE 7

Table 7 comprises 145 compounds of formula (Ii) wherein Z is CH and X has the value listed for the correspondingly numbered compound in Table 1.

TABLE 8

Table 8 comprises 145 compounds of formula (Ii) wherein Z is N and X has the value listed for the corresponding numbered compound in Table 1.

TABLE I

Table I shows melting point or selected proton NMR data for certain compounds described in the Tables above.

Chemical shifts are measured in ppm from tetramethylsilane, and deuterochloroform was used as solvent. Unless otherwise stated, spectra were recorded on an instrument operating at 270 MHz. The following abbreviations are used:

| | |
|---|---|
| s = singlet | d = doublet |
| t = triplet | m = multiplet |
| q = quartet | dd = double doublet |
| br = broad | ppm = parts per million |
| td = triple doublets | |

| Compound No. (Table No.) | Data |
|---|---|
| 2(1) | 3.74(3H, s); 7.01(1H, s); 6.90–7.05(4H, m); 7.15–7.35 (4H, m); 7.30(1H, s); 7.42(1H, dd); 7.46(1H, s)ppm. |
| 2(2) | A mixture of stereoisomers about Q—C=Z.OCH$_3$ bond. Stereoisomer A: 4.15(3H, s); 6.82–6.90(3H, m); 7.05 (1H, t); 7.16–7.28(3H, m); 7.22(1H, s); 7.38(1H, td); 7.60(1H, s); 7.62(1H, dd)ppm. Stereoisomer B: 4.00(3H, s); 6.95–7.00(3H, m); 7.05 (1H, t); 7.20(1H, s); 7.18–7.33(3H, m); 7.35–7.42 (2H, m); 7.68(1H, s)ppm. |
| 1(3) | 16:9 (E):(Z) Mixture of stereoisomers about Q—C=Z.OCH$_3$ bond. (E)-isomer: 2.20(3H, s); 3.88(3H, s); 7.20–7.32(4H, m); 7.50(1H, s); 8.23(1H, s)ppm. (Z)-isomer: 2.18(3H, s); 4.00(3H, s); 6.61(1H, s); 7.20–7.32(4H, m); 8.30(1H, s)ppm. |
| 2(3) | 3.80(3H, s); 6.90(1H, d); 6.96(1H, d); 7.03(1H, t); 7.15–7.36(4H, m); 7.42(1H, s); 7.44(1H, dd); 8.20 (1H, s)ppm. |
| 1(4) | 69° C. |
| 2(4) | Mixture of stereoisomers about Q—C=Z.OCH$_3$ bond. Stereoisomer A: 4.15(3H, s); 6.83(3H, d); 7.07(1H, t); 7.15–7.30(3H, m); 7.39(1H, td); 7.71(1H, dd); 8.35 (1H, s)ppm. 17:3 B:A mixture of stereoisomers about QC=Z.OCH$_3$ bond. 4.07(3H, s); 6.92–7.12(3H, m); 7.08(1H, t); 7.16–7.32 (3H, m); 7.35–7.45(2H, m); 8.40(1H, s)ppm. |
| 35(4) | 96–97° C. |
| 63(4) | 2.10(3H, s); 4.05(3H, s); 5.15(2H, s); 7.30(1H, d); 7.40–7.60(5H, m); 7.70(1H, d); 7.80(1H, s); 8.40 (1H, s)ppm. |
| 92(4) | 4.10(3H, s); 5.45(2H, s); 6.65(1H, d); 6.90–7.00(1H, dd); 7.20(1H, d); 7.35(1H, dd); 7.50(2H, m); 7.65(2H, t); 8.45(1H, s)ppm. |
| 99(4) | 1.35(6H, d); 2.15(3H, s); 4.10(3H, s); 5.30(2H, s); 5.40 (1H, m); 6.60(1H, d); 7.30(1H, d); 7.50(2H, m); 7.60(1H, d); 8.50(s and d overlapping, 2H)ppm. |
| 1(6) | (E)-Stereoisomer about Q—C=Z.OCH$_3$ bond; 2.25(3H, s); 4.20(3H, s); 7.25(2H, m); 7.30(2H, m); 8.80(1H, s)ppm. (Z)-Stereoisomer about Q—C=Z.OCH$_3$ bond; 2.20(3H, s); 4.10(3H, s); 7.20–7.40(4H, m); 8.70(1H, s)ppm. |
| 35(6) | Stereoisomer A about Q—C=Z.OCH$_3$ bond, 65–66° C. Stereoisomer B about Q—C=Z.OCH$_3$ bond, 2.20(3H, s); 4.10(3H, s); 5.00(2H, s); 6.75(1H, d); 6.85(1H, t); 7.10(2H, m); 7.30(1H, d); 7.5(2H, m); 7.70(1H, d); 8.80(1H, s)ppm. |
| 62(6) | 94–95° C. |
| 92(6) | 4.10(3H, s); 5.40(2H, s); 6.70(1H, d); 7.20(1H, d); 7.30(1H, dd); 7.50(2H, m); 7.65(2H, t); 8.75(1H, s)ppm. |
| 35(8) | 2.1(3H, s); 4.10(3H, s); 5.00(2H, s); 6.70(1H, d); 6.85(1H, t); 7.10(2H, t); 7.30(1H, d); 7.45(1H, t); 7.50(1H, t); 7.65(1H, d); 8.45(1H, s)ppm. |

The compounds of the invention of formula (I) may be prepared by the pathway shown in Scheme 1 or, when Z is N, by the pathways shown in Schemes 2, 3 and 4. Throughout these Schemes, the terms Q, Z and A are as defined above, M is hydrogen or a metal (such as sodium), R is an alkyl group and X' is either equivalent to X as defined above or is a group which may be converted into X. Each reaction shown in Schemes 1 to 4 is performed either in a suitable solvent or without a solvent, and at a suitable temperature.

The use of the term X' in Schemes 1 to 4 illustrates that the group X of the compounds of the invention of formula (I) may be constructed at various points in the synthetic sequence. Thus it may be constructed at an early stage of the synthesis, in which case X' is equivalent to X in each of the Schemes 1 to 4. Or it may be constructed during the last step or steps of the synthesis, in which case, in each of the Schemes 1 to 4, X' is a group which may be converted into X. Alternatively, the group X may be constructed at any suitable intermediate stage of the sequences shown in Schemes 1 to 4.

Thus compounds (Ia) may be prepared by methylation of compounds of formula (III) using a methylating agent such as a methyl halide (for example, methyl iodide) or dimethyl sulphate (Scheme 1). When M is hydrogen, this reaction is generally performed in the presence of a base such as potassium carbonate. When M is a metal (preferably an alkali metal such as sodium or potassium), the addition of a base is not necessary.

Compounds (III) wherein Z is CH (which may exist in equilibrium with the tautomeric formyl compounds) may be prepared by treatment of compounds of formula (II) with an alkyl formate (such as methyl or ethyl formate) in the presence of a base (such as sodium hydride). The group M is a metal in compounds formed in this way, but the corresponding compounds wherein M is hydrogen are formed if the reaction mixture is acidified before work-up, or if the compounds (III) wherein M is a metal are treated with a suitable acid such as a mineral acid in a subsequent step.

Compounds (III) wherein Z is N may be prepared by nitrosation of compounds (II) under either basic or acidic conditions. For example, treatment of compounds (II) with an alkyl nitrite (such as isoamyl nitrite) in the presence of a base (such as sodium hydride) leads to compounds (III) wherein M is a metal, which may be converted by treatment with a suitable acid into compounds (III) wherein M is hydrogen.

Compounds of formula (II) may be prepared from appropriate alkyl phenylacetates, phenylacetyl chlorides or phenylacetonitriles using methods which parallel those shown in Schemes 2, 3 and 4 respectively. The required alkyl phenylacetates, phenylacetyl chlorides and phenylacetonitriles may, in turn, be prepared by standard methods described in the chemical literature.

In an alternative procedure, compounds of the invention of formula (Ia) may be prepared from ketones of formula (IV) (Scheme 1). Compounds (Ia) wherein Z is CH may be prepared by treatment of ketones (IV) with the Wittig reagent methoxymethylenetriphenylphosphorane or an equivalent reagent. Compounds (Ia) wherein Z is nitrogen may be prepared by treatment of ketones (IV) with methoxylamine [or with hydroxylamine, which gives compounds (III) wherein Z is nitrogen and M is hydrogen, which may in turn be converted by methylation as described above into the compounds (Ia)].

Ketones of formula (IV) may be prepared by oxidation of compounds of formula (II) or by various other methods based on chemistry described in the literature. For example, treatment of 2-formyl-oxazole (see *J. Organic Chemistry*, 1991, 56, 449) with appropriate Grignard reagents and oxidation of the resulting secondary alcohols produces ketones of formula (IV) in which Q is 2-oxazolyl.

1,3,4-Oxadiazoles of the invention wherein Z is nitrogen of formula (Ib) may be prepared by treatment of hydrazides of formula (V) with a trialkyl orthoformate (such as trimethyl orthoformate) under acidic conditions (Scheme 2). The hydrazides (V) may themselves be prepared by treatment of esters of formula (VI) with hydrazine. The esters (VI) may be prepared by methods described in the chemical literature (see, for example, EP 254426).

5-Substituted 1,2,4-oxadiazoles of the invention wherein Z is nitrogen of formula (Ic) (Scheme 3) may be prepared by treatment of acid chlorides of formula (VIII) with formamide oxime ($H_2NCH=NOH$) in the presence of a base (such as triethylamine) according to methods described in the chemical literature (see, for example, JP 61063668= *Chemical Abstracts*, 105, 172470f) (Scheme 3). Acid chlorides (VIII) may be prepared by conventional methods from acids of formula (VII) which may, in turn, be prepared by hydrolysis of esters of formula (VI) under basic conditions. 5-Substituted 1,2,4-oxadiazoles of the invention may also be prepared by other methods described in the chemical literature. For example, treatment of acid chlorides of formula (VIII) with ammonia under standard conditions gives the corresponding amides, which are converted on successive treatment with dimethylformamide dimethyl acetal and hydroxylamine under conditions such as those described by Yang-i Lin et al. in *J. Organic Chemistry*, 1979, 44, 4160 into 5-substituted 1,2,4-oxadiazoles (Ic).

3-Substituted 1,2,4-oxadiazoles of the invention wherein Z is nitrogen of formula (Id) (Scheme 4) may be prepared by treatment of amidoximes of formula (IX) with a trial kyl orthoformate (such as trimethyl orthoformate) under acidic conditions. Amidoximes (IX) may, in turn, be prepared by treatment of nitriles of formula (X) with hydroxylamine. Nitriles (X) may be prepared by successive nitrosation and O-methylation of phenylacetonitriles (XI) using methods which parallel those described above for the conversion of (II) into (III) wherein Z is nitrogen. Alternatively, they may be prepared by dehydration of the corresponding primary amides as described in EP 528681. Nitriles related to (X) have been described in EP 0477631. Phenylacetonitriles (XI) may be prepared by standard methods described in the chemical literature.

Compounds of the invention of formula (Ij), wherein Y' is optionally substituted aryloxy, optionally substituted arylthio, optionally substituted heteroaryloxy, optionally substituted heteroarylthio or $R^1R^2C=NO$, can be made as shown in Scheme 5 from compounds of formula (XIII) wherein V is halogen (such as chlorine, bromine or iodine). Thus compounds of formula (XII) can for example be brominated, with, for example, bromine or N-bromosuccinimide while being illuminated by a strong light source, and in the presence of an initiator such as dibenzoyl peroxide or azo-bis(iso-butyronitrile), to produce compounds of formula (XIII) wherein V is bromine. Compounds of formula (XIII) wherein V is chlorine or iodine can be made from compounds of formula (XIII) wherein V is bromine by reaction with a metal chloride (for example lithium chloride) or a metal iodide (for example sodium iodide). Compounds of formula (XIII) can then be reacted with an optionally substituted hydroxyaryl, optionally substituted arylthiol, optionally substituted hydroxyheteroaryl, optionally substituted heteroarylthiol or oxime of structure $R^1R^2C=NOH$ in the presence of a base such as sodium hydride or potassium carbonate in a solvent such as N,N-dimethylformamide or tetrahydrofuran, to give the compounds of the invention of formula (Ij).

Compounds of the invention of formula (Ik) may be made as shown in Scheme 6. Thus a compound of formula (XIV)

may be converted to an acid of formula (XV) by careful hydrolysis with an alkali metal hydroxide in a solvent (such as water or aqueous methanol), or alternatively by a demethylation method (such as heating with lithium iodide in pyridine). The acid (XV) can then be reacted with a chlorinating agent (such as thionyl chloride) to form the acid chloride of formula (XVI). Compounds of formula (XVII) can be made from compounds (XVI) by reaction with hydrazine in the presence of a base (such as triethylamine). Compounds (XVII) can be converted to compounds of formula (Ik) by reaction with a trialkyl orthoformate (such as trimethyl orthoformate) under acidic conditions.

Alternatively compounds (XVI) can be reacted with formylhydrazine, in the presence of a base (such as triethylamine) to give compounds of formula (XVIII). Compounds (XVIII) can then be reacted with an acidic catalyst (such as para-toluenesulphonic acid) to give compounds of formula (Ik).

In further aspects the present invention comprises processes for preparing the compounds of formula (I) and intermediate compounds of formula (XIII).

The compounds are active fungicides and may be used to control one or more of the following pathogens: *Pyricularia oryzae* on rice and wheat and other Pyricularia spp. on other hosts; *Puccinia recondita, Puccinia striiformis* and other rusts on wheat, *Puccinia hordei, Puccinia striiformis* and other rusts on barley, and rusts on other hosts e.g. turf, rye, coffee, pears, apples, peanuts, sugar beet, vegetables and ornamental plants; *Erysiphe graminis* (powdery mildew) on barley, wheat, rye and turf and other powdery mildews on various hosts such as *Sphaerotheca macularis* on hops, *Sphaerotheca fuliginea* on cucurbits (e.g. cucumber), *Podosphaera leucotricha* on apple and *Uncinula necator* on vines; Cochliobolus spp., Helminthosporium spp., Drechslera spp. (Pyrenophora spp.), Rhynchosporium spp., Septoria spp. (including *Mycosphaerella graminicola* and *Leptosphaeria nodorum*), *Pseudocercosporella herpotrichoides* and *Gaeumannomyces graminis* on cereals (e.g. wheat, barley, rye), turf and other hosts; *Cercospora arachidicola* and *Cercosporidium personarum* on peanuts and other Cercospora species on other hosts, for example, sugar beet, bananas, soya beans and rice; *Botrytis cinerea* (grey mould) on tomatoes, strawberries, vegetables, vines and other hosts and other Botrytis spp. on other hosts; Alternaria spp. on vegetables (e.g. cucumber), oil-seed rape, apples, tomatoes, cereals (e.g. wheat) and other hosts; Venturia spp. (including *Venturia inaequalis* (scab)) on apples, pears, stone fruit, tree nuts and other hosts; Cladosporium spp. on a range of hosts including cereals (e.g. wheat); Monilinia spp. on stone fruit, tree nuts and other hosts; Didymella spp. on tomatoes, turf, wheat and other hosts; Phoma spp. on oil-seed rape, turf, rice, potatoes, wheat and other hosts; Aspergillus spp. and Aureobasidium spp. on wheat, lumber and other hosts; Ascochyta spp. on peas, wheat, barley and other hosts; *Plasmopara viticola* on vines; other downy mildews such as *Bremia lactucae* on lettuce, Peronospora spp. on soybeans, tobacco, onions and other hosts, *Pseudoperonospora humuli* on hops and *Pseudoperonospora cubensis* on cucurbits; Pythium spp. on turf and other hosts; *Phytophthora infestans* on potatoes and tomatoes and other Phytophthora spp. on vegetables, strawberries, avocado, pepper, ornamentals, tobacco, cocoa and other hosts; *Thanatephorus cucumeris* on rice and turf and other Rhizoctonia species on various hosts such as wheat and barley, vegetables, cotton and turf; Sclerotinia spp. on turf, peanuts, oil-seed rape and other hosts; Sclerotium spp. on turf, peanuts and other hosts; Colletotrichum spp. on a range of hosts including turf, coffee and vegetables; *Laetisaria fuciformis* on turf; Mycosphaerella spp. on banana, peanut, citrus, pecan, papaya and other hosts; Diaporthe spp. on citrus, soybean, melon, pear, lupin and other hosts; Elsinoe spp. on citrus, vines, olives, pecans, roses and other hosts; Pyrenopeziza spp. on oil-seed rape and other hosts; *Oncobasidium theobromae* on cocoa causing vascular streak dieback; Fusarium spp., Typhula spp., *Microdochium nivale*, Ustilago spp., Urocystis spp., Tilletia spp., and *Claviceps purpurea* on a variety of hosts but particularly wheat, barley, turf and maize; Ramularia spp. on sugar beet and other hosts; post-harvest diseases particularly of fruit (e.g. *Pencillium digitatum* and *P. italicum* and *Trichoderma viride* on oranges, *Colletotrichum musae* and *Gloeosporium musarum* on bananas and *Botrytis cinerea* on grapes); other pathogens on vines, notably *Eutypa lata*, *Guignardia bidwellii*, *Phellinus igniarus*, *Phomopsis viticola*, *Pseudopezicula tracheiphila* and *Stereum hirsutum*; other pathogens on lumber, notably *Cephaloascus fragrans*, Ceratocystis spp., *Ophiostoma piceae*, Penicillium spp., *Trichoderma pseudokoningii*, *Trichoderma viride Trichoderma harzianum*, *Aspergillus niger*, *Leptographium lindbergi* and *Aureobasidium pullulans*; and fungal vectors of viral diseases e.g. *Polymyxa graminis* on cereals as the vector of barley yellow mosaic virus (BYMV). The compounds are especially useful for combating fungal disease on rice (such as *Pyricularia oryzae*).

Some of the compositions show a broad range of activities against fungi in vitro.

Further, some of the compositions may be active as seed dressings against pathogens including Fusarium spp., Septoria spp., Tilletia spp., (e.g. bunt, a seed-borne disease of wheat), Ustilaqo spp. and Helminthosporium spp. on cereals, *Rhizoctonia solani* on cotton and *Pyricularia oryzae* on rice.

The compounds may move acropetally/locally in plant tissue. Moreover, the compounds may be volatile enough to be active in the vapour phase against fungi on the plant.

The invention therefore provides a method of combating fungi which comprises applying to a plant, to a seed of a plant or to the locus of the plant or seed a fungicidally effective amount of a compound as hereinbefore defined, or a composition containing the same.

The compounds may be used directly for agricultural purposes but are more conveniently formulated into compositions using a carrier or diluent. The invention thus provides fungicidal compositions comprising a compound as hereinbefore defined and an acceptable carrier or diluent therefor. It is preferred that all compositions, both solid and liquid formulations, comprise 0.0001 to 95%, more preferably 1 to 85%, for example 1 to 25% or 25 to 60%, of a compound as hereinbefore defined.

When applied the foliage of plants, the compounds of the invention are applied at rates of 0.1 g to 10 kg, preferably 1 g to 8 kg, more preferably 10 g to 4 kg, of active ingredient (invention compound) per hectare.

When used as seed dressings, the compounds of the invention are used at rates of 0.0001g (for example 0.001 g or 0.05 g) to 10 g, preferably 0.005 g to 8 g, more preferably 0.005 g to 4 g, of active ingredient (invention compound) per kilogram of seed.

The compounds can be applied in a number of ways. For example, they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules.

Application can be to any part of the plant including the foliage, stems, branches or roots, or to soil surrounding the roots, or to the seed before it is planted, or to the soil generally, to paddy water or to hydroponic culture systems. The invention compounds may also be injected into plants or sprayed onto vegetation using electrodynamic spraying techniques or other low volume methods, or applied by land or aerial irrigation systems.

The term "plant" as used herein includes seedlings, bushes and trees. Furthermore, the fungicidal method of the invention includes preventative, protectant, prophylactic, systemic and eradicant treatments.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example, fillers such as kaolin, bentonire, kieselguhr, dolomite, calcium carbonate, talc, powdered magnesia, fuller's earth, gypsum, diatomaceous earth and china clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example, a mineral oil) for assisting the adhesion of the composition to the seed; alternatively the active ingredient can be formulated for seed dressing purposes using an organic solvent (for example, N-methylpyrrolidone, propylene glycol or N,N-dimethylformamide). The compositions may also be in the form of water dispersible powders or water dispersible granules comprising wetting or dispersing agents to facilitate the dispersion in liquids. The powders and granules may also contain fillers and suspending agents.

The compositions may also be in the form of soluble powders or granules, or in the form of solutions in polar solvents.

Soluble powders may be prepared by mixing the active ingredient with a water-soluble salt such as sodium bicarbonate, sodium carbonate, magnesium sulphate or a polysaccharide, and a wetting or dispersing agent to improve water dispersibility/solubility. The mixture may then be ground to a fine powder. Similar compositions may also be granulated to form water-soluble granules. Solutions may be prepared by dissolving the active ingredient in polar solvents such as ketones, alcohols and glycol ethers. These solutions may contain surface active agents to improve water dilution and prevent crystallisation in a spray tank.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as cyclohexanone and methylcyclohexanone, chlorinated hydrocarbons such as chlorobenzene and trichlorethane, and alcohols such as benzyl alcohol, furfuryl alcohol, butanol and glycol ethers.

Aqueous suspension concentrates of largely insoluble solids may be prepared by ball or bead milling with a dispersing agent with a suspending agent included to stop the solid settling.

Compositions to be used as sprays may be in the form of aerosols wherein the formulation is held in a container under pressure of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the uptake, distribution, adhesive power and resistance to rain on treated surfaces, the different compositions can be better adapted for various utilities. Other additives may be included to improve the biological efficacy of the various formulations. Such additives can be surface active materials to improve the wetting and retention on surfaces treated with the formulation and also the uptake and mobility of the active material, or additionally can include oil based spray additives, for example, certain mineral oil and natural plant oil (such as soya bean and rape seed oil) additives, or blends of them with other adjuvants.

The invention compounds can be used as mixtures with fertilisers (e.g. nitrogen-, potassium- or phosphorus-containing fertilisers). Compositions comprising only granules of fertiliser incorporating, for example coated with, a compound of formula (I) are preferred. Such granules suitably contain up to 25% by weight of the compound. The invention therefore also provides a fertiliser composition comprising a fertiliser and the compound of general formula (I) or a salt or metal complex thereof.

Water dispersible powders, emulsifiable concentrates and suspension concentrates will normally contain surfactants, e.g. a wetting agent, dispersing agent, emulsifying agent or suspending agent. These agents can be cationic, anionic or non-ionic agents.

Suitable cationic agents are quaternary ammonium compounds, for example, cetyltrimethylammonium bromide. Suitable anionic agents are soaps, salts of aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, alkyl glucosides, polysaccharides and the lecithins and the condensation products of the said partial esters with ethylene oxide. Suitable suspending agents are hydrophilic colloids (for example, polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 1–85%, for example 1–25% or 25–60%, by weight of the active ingredient. After dilution to form aqueous preparations, such preparations may contain varying amounts of the active ingredient depending upon the intended purpose, but an aqueous preparation containing 0.0001 to 10%, for example 0.005 to 10%, by weight of active ingredient may be used.

The compositions of this invention may contain other compounds having biological activity, e.g. compounds having similar or complementary fungicidal activity or which possess plant growth regulating, herbicidal or insecticidal activity.

By including another fungicide, the resulting composition can have a broader spectrum of activity or a greater level of intrinsic activity than the compound of general formula (I) alone. Further the other fungicide can have a synergistic effect on the fungicidal activity of the compound of general formula (I). Examples of fungicidal compounds which may be included in the composition of the invehtion are (RS)-1-aminopropylphosphonic acid, (RS)-4-(4-chlorophenyl)-2-phenyl-2-(1H-1,2,4-triazol-1-yl-methyl) butyronitrile, (Z)-N-but-2-enyloxymethyl-2-chloro-2', 6'-diethylacetanilide, 1-(2-cyano-2-methoxyiminoacetyl)-3-ethyl urea, 4-(2,2-difluoro-1,3-benzodioxol-4-yl)pyrrole-3-carbonitrile, 4-bromo-2-cyano-N,N-dimethyl-6-trifluoromethylbenzimidazole-1-sulphonamide, 5-ethyl-5,8-dihydro-8-oxo(1,3)-dioxol-(4,5-g)quinoline-7-carboxylic acid, α-[N-(3-chloro-2,6-xylyl)-2-methoxyacetamido]-g-butyrolactone, N-(2-methoxy-5-pyridyl)-cyclopropane carboxamide, alanycarb, aldimorph, ampropylfos, anilazine, azaconazole, BAS 490F, benalaxyl, benomyl, biloxazol, binapacryl, bitertanol, blasticidin S, bromuconazole, bupirimate, butenachlor, buthiobate, captafol, captan, carbendazim, carbendazim chlorhydrate, carboxin, chinomethionate, chlorbenzthiazone, chloroneb, chlorothalonil, chlorozolinate, clozylacon, copper containing compounds such as copper oxychloride, copper oxyquinolate, copper sulphate, copper tallate, and Bordeaux mixture, cycloheximide, cymoxanil, cyproconazole, cyprofuram, debacarb, di-2-pyridyl disulphide 1,1'-dioxide, dichlofluanid, dichlone, diclobutrazol, diclomezine, dicloran, didecyl dimethyl ammonium chloride, diethofencarb, difenoconazole, O,O-di-iso-propyl-S-benzyl thiophosphate, dimefluazole, dimetconazole, dimethomorph, dimethirimol, diniconazole, dinocap, dipyrithione, ditalimfos, dithianon, dodemorph, dodine, doguadine, edifenphos, epoxiconazole, etaconazole, ethirimol, ethoxyquin, ethyl (Z)-N-benzyl-N-([methyl (methyl-thioethylideneamino-oxycarbonyl)amino]thio)-β-alaninate, etridiazole, fenaminosulph, fenapanil, fenarimol, fenbuconazole, fenfuram, fenpiclonil, fenpropidin, fenpropimorph, fentin acetate, fentin hydroxide, ferbam, ferimzone, fluazinam, fludioxonil, fluoroimide, fluquinconazole, flusilazole, flutolanil, flutriafol, folpet, fuberidazole, furalaxyl, furconazole-cis, guazatine, hexaconazole, hydroxyisoxazole, hymexazole, ICIA5504, imazalil, imibenconazole, ipconazole, iprobenfos, iprodione, isopropanyl butyl carbamate, isoprothiolane, kasugamycin, mancozeb, maneb, mepanipyrim, mepronil, metalaxyl, metconazole, methfuroxam, metiram, metiram-zinc, metsulfovax, myclobutanil, neoasozin, nickel dimethyldithiocarbamate, nitrothal-iso-propyl, nuarimol, ofurace, organomercury compounds, oxadixyl, oxolinic acid, oxycarboxin, pefurazoate, penconazole, pencycuron, phenazin oxide, phosetyl-Al, phosphorus acids, phthalide, polyoxin D, polyram, probenazole, prochloraz, procymidone, propamocarb, propamocarb hydrochloride, propiconazole, propineb, propionic acid, prothiocarb, pyracarbolid, pyrazophos, pyrifenox, pyrimethanil, pyroquilon, pyroxyfur, pyrrolnitrin, quaternary ammonium compounds, quinconazole, quinomethionate, quintozene, rabenazole, sodium pentachlorophenate, streptomycin, sulphur, tebuconazole, techlofthalam, tecnazene, tetraconazole, thiabendazole, thicyofen, thifluzamide, 2-(thiocyanomethylthio)benzothiazole, thiophanate-methyl, thiram, timibenconazole, tolclofos-methyl, tolylfluanid, triacetate salt of 1,1'-iminodi(octamethylene)diguanidine, triadimefon, triadimenol, triazbutyl, triazoxide, tricyclazole, tridemorph, triforine, triflumizole, triticonazole, validamycin A, vapam, vinclozolin, XRD-563, zineb and ziram. The compounds of general formula (I) can be mixed with soil, peat or other rooting media for the protection of plants against seed-borne, soil-borne or foliar fungal diseases.

The following Examples illustrate the invention. In the Examples, the term 'ether' referes to diethyl ether, anhydrous magnesium sulphate was used to dry solutions, and solutions were concentrated under reduced pressure. Reactions involving air- or water-sensitive intermediates were performed under an atmosphere of nitrogen and solvents were dried before use, where appropriate. Unless otherwise stated, chromatography was performed on a column of silica gel as the stationary phase. NMR data are selective; no attempt is made to list every absorption. $^1$H NMR spectra were recorded using $CDCl_3$-solutions on an instrument operating at 270 MHz, unless otherwise stated. The following abbreviations are used:

| | |
|---|---|
| DMSO = dimethylsulphoxide | s = singlet |
| DMF = N,N-dimethylformamide | d = doublet |
| NMR = nuclear magnetic resonance | m = multiplet |
| IR = infrared | mp = melting point |
| GC = Gas chromatography | ppm = parts per million |
| TLC = Thin layer chromatography | |

EXAMPLE 1

This Example illustrates the preparation of (E)-2-[1-(2-phenoxyphenyl)-2-methoxyvinyl]oxazole (Compound No. 2 of Table 1).

A mixture of (2-phenoxyphenyl)acetamide (3.9 g) and bromoacetaldehyde diethyl acetal (3.1 ml) in DMF (100 ml) was heated for 2 hours. After cooling, the resulting mixture was diluted with water and extracted with ether. The extracts were washed with water then dried, concentrated and chromatographed using ethyl acetate: hexane (50:50) as eluant to give 2-(2-phenoxyphenylmethyl)oxazole (1.77 g, 41%) as a brown oil, $^1$H NMR ($CDCl_3$): delta 4.20 (2H,s), 7.01 (1H,s) and 7.54 (1H,s) ppm.

A solution of 2-(2-phenoxyphenylmethyl)oxazole (500 mg) in methyl formate (2 ml) and DMF was added to a stirred suspension of sodium hydride (96 mg) in DMF (total volume of DMF=20 ml). The resulting mixture was stirred at room temperature for 3 hours. Further methyl formate (5 ml) was added and the reaction mixture was heated at 50° C. for 3 hours then allowed to cool. Water was added and the resulting mixture was acidified and extracted with ether. The ether extracts were washed with water, dried and concentrated to give a yellow gum (560 mg). A mixture of this gum, dimethyl sulphate (0.42 ml) and potassium carbonate (550 mg) in DMF (10 ml) was stirred at room temperature for 3 hours then diluted with water and extracted with ether. The extracts were washed with water, dried, concentrated and chromatographed using ethyl acetate: hexane (20:80) as eluant to give the title compound [110 mg, 19% yield from 2-(2-phenoxyphenylmethyl)oxazole] as an orange gum, ¹H NMR (CDCl₃): delta 3.74 (3H,s), 7.01 (1H,s), 7.30 (1H,s, olefinic proton—assignment confirmed by nuclear Overhauser enhancement with methoxy protons) and 7.46 (1H,s) ppm.

EXAMPLE 2

This Example illustrates the preparation of (E)-2-[1-(2-phenoxyphenyl)-2 2-methoxyvinyl]oxa-1,3,4-diazole (Compound No. 2 of Table 3).

A solution of methyl (2-phenoxyphenyl)acetate (6.0 g) in methanol (100 ml) was added dropwise with stirring to hydrazine hydrate (12 ml). The resulting mixture was stirred for 2 hours, then diluted with water and extracted with ether. The extracts were washed with water, dried and concentrated to give almost pure (2-phenoxyphenyl)acetohydrazide (5.8 g, 96% yield) as a waxy solid with amp of about 65° C., ¹H NMR (CDCl₃): delta 3.60 (2H,s) ppm. Concentrated sulphuric acid (4 drops) was added to a mixture of this hydrazide and triethyl orthoformate (20 ml) and the resulting mixture was heated at 90° C. for one hour. After cooling, water was added to the mixture and it was extracted with ether. The extracts were washed, dried, concentrated and chromatographed using increasing proportions (up to 50%) of ethyl acetate in hexane as eluant to give 2-(2-phenoxyphenylmethyl)oxa-1,3,4-diazole (3.14 g, 52% yield) as a yellow oil, ¹H NMR (CDCl₃): delta 4.31 (2H,s) and 8.28 (1H,s) ppm.

A solution of 2-(2-phenoxyphenylmethyl)oxa-1,3,4-diazole (500 mg) in methyl formate (10 ml) and DMF was added to a stirred suspension of sodium hydride (96 mg) in DMF (total volume of DMF=20 ml). The resulting mixture was stirred for 3 hours at room temperature, then heated at 45° C. for 1.5 hours, then allowed to cool. Water was added and the resulting mixture was acidified and extracted with ether. The extracts were washed with water, dried and concentrated. The residue was dissolved in DMF (20 ml) and potassium carbonate (550 mg) was added with stirring. After 15 minutes, dimethyl sulphate (2 ml) was added and the mixture was stirred for 2 hours. Water was added and the resulting mixture was extracted with ether. The extracts were washed with water, dried, concentrated and chromatographed in ethyl acetate: hexane (20:80) to give the title compound [170 mg, 29% yield from 2-(2-phenoxybenylmethyl)oxa-1,3,4-diazole] as a yellow gum, ¹H NMR (CDCl₃): delta 3.80 (3H,s), 7.42 (1H,s) and 8.20 (1H,s) ppm.

EXAMPLE 3

This Example illustrates the preparation of the two stereoisomers of 2-(2-phenoxybenzoyl)oxa-1,3,4-diazole O-methyloxime (Compound No. 2 of Table 4).

A solution of 2-(2-phenoxyphenytmethyl)oxa-1,3,4-diazole (1.0 g, prepared as described in Example 2) in DMF was added dropwise to a stirred suspension of sodium hydride (115 mg) in DMF (total volume of DMF=30 ml). After 30 minutes, t-butyl nitrite (0.57 ml) was added. After a further 3 hours, water was added and the resulting mixture was acidified and extracted with ether. The extracts were washed with water, dried, concentrated and chromatographed using ethyl acetate: hexane (50:50) as eluant to give, in order of elution, (i) a 9:1 mixture of stereoisomers of 2-phenoxybenzoyl cyanide oxime (390 mg, 41% yield) as a yellow gum; (ii) isomer A of 2-(2-phenoxybenzoyl)oxa-1,3,4-diazole oxime (200 mg, 18% yield) as a white solid, mp 120°–3° C., ¹H NMR (CDCl₃): delta 8.39 (1H,s) and 10.89 (1H,br s) ppm; and (iii) a 1:9 mixture, respectively, of isomers A and B of 2-(2-phenoxybenzoyl)oxa-1,3,4-diazole oxime (180 mg, 16% yield) as a white solid, softening at 55° C. and melting at about 115° C., ¹H NMR (CDCl₃) for isomer B: delta 8.41 (1H,s) and 9.64 (1H,br s) ppm. A mixture of part of the sample of isomer A of 2-(2-phenoxybenzoyl)-oxa-1,3,4-diazole oxime (150 mg) and potassium carbonate (150 mg) in DMF (5 ml) was stirred at room temperature. After 15 minutes, dimethyl sulphate (0.2 ml) was added. The reaction mixture was stirred for 2 hours, then poured into water and extracted with ether. The extracts were washed with water, dried, concentrated and chromatographed using ethyl acetate: hexane (20:80) as eluant to give isomer A of the title compound (110 mg, 70% yield) as a yellow gum, ¹H NMR (CDCl₃): delta 4.15 (3H,s) and 8.35 (1H,s) ppm. The 1:9 mixture of isomers A and B, respectively, of 2-(2-phenoxybenzoyl)oxa-1,3,4-diazole oxime was O-methylated by the same procedure to give a 66% yield of a 3:17 mixture, respectively, of isomers A and B of the title compound as a colourless gum, ¹H NMR (CDCl₃) for isomer B: delta 4.07 and 8.40 (1H,s) ppm.

EXAMPLE 4

This Example illustrates the preparation of (E,E)-2-[2-([3-trifluoromethylphenyl]acetoximinomethyl)benzoyl]oxa-1,3,4-diazole O-methyloxime (Compound No. 62 of Table 4).

A solution of (E,E)-methyl 3-methoxy-2-[2-([3-trifluoromethylphenyl]-acetoximinomethyl) phenyl] propenoate (250 mg, prepared from 3-trifluoromethylacetophenone oxime and (E)-methyl 2-[2-(bromomethyl)phenyl]-3-methoxypropenoate by the method described in EP 370629 for the preparation of related compounds) in methanol (5 ml) was added to hydrazine hydrate with stirring. The resulting mixture was stirred for 5 hours, then concentrated and chromatographed using ethyl acetate as eluant to give (E,E)-3-methoxy-2-[2-([3-trifluoromethylphenyl]acetoximinomethyl)phenyl] propenohydrazide (180 mg, 72% yield) as a solid, ¹H NMR (CDCl₃): delta 2.2 (3H,s), 3.95 (3H,s), 5.15 (2H,s) ppm.

A mixture of the hydrazide from the previous step (170 mg), triethyl orthoformate (4 ml) and concentrated sulphuric acid (2 drops) was heated under reflux for 6 hours, then allowed to cool and concentrated. The residue was chromatographed twice, using first ethyl acetate and then ethyl acetate:hexane (50:50) as eluant. Fractions containing the title compound were dissolved in ethyl acetate then washed with aqueous ammonium chloride, dried and concentrated, and the residue was again chromatographed using ethyl acetate:hexane (20:80) to give the title compound (24 mg, 13% yield) as an oil, ¹H NMR (CDCl₃):delta 2.1 (3H,s), 4.05 (3H,s), 5.15 (2H,s) and 8.4 (1H,s) ppm.

EXAMPLE 5

This Example illustrates the preparation of both stereoisomers of 3-[2-(2-methylphenoxymethyl)benzoyl]oxa-1,2,4-diazole O-methyloxime (Compound No. 35 of Table 6).

A solution of sodium ethoxide [prepared from sodium (6.0 g) and ethanol] was added dropwise over 45 minutes to a stirred solution of (2-methylphenyl)acetonitrile (23.2 g) and isoamyl nitrite (90 ml) in ethanol (total volume of ethanol=400 ml) (exotherm). The resulting mixture was stirred for 6 hours, allowed to stand overnight, then concentrated. Water was added to the residue and it was washed with ether. The aqueous layer was then acidified with dilute hydrochloric acid and extracted with ether. The ether extracts were washed with water, dried and concentrated. Potassium carbonate (50 g) was added to a solution of the residue in THF (150 ml) and the mixture was heated at reflux for i hour and allowed to cool. Dimethyl sulphate (3 ml) was added over 1 hour and the resulting mixture was stirred for 4 hours at room temperature and then allowed to stand over a weekend. The reaction mixture was poured into water and extracted with ether. The extracts were washed with water, dried, concentrated, flushed through a column of silica gel with dichloromethane then concentrated to give a yellow liquid (28.5 g). Purification of this liquid by chromatography using dichloromethane as eluant then gave 2-methylbenzoyl cyanide O-methyloxime [22 g, 71% yield from (2-methylphenyl)-acetonitrile] as an oil, a mixture of stereoisomers in which one isomer strongly predominated, $^1$H NMR (CDCl$_3$) for the major isomer: δ 2.65 (3H,s) and 4.4 (3H,s) ppm; and for the minor isomer: δ 2.3 (3H,s) and 4.05 (3H,s) ppm.

Part of the mixture of stereoisomers of 2-methylbenzoyl cyanide O-methyloxime (8.7 g) was dissolved in a 2.7 Molar solution of bromine in carbon tetrachloride (20 ml) and the resulting solution was heated under illumination and at reflux for 2 hours, then allowed to cool. The reaction mixture was washed with aqueous sodium metabisulphite, then dried and concentrated to give a mobile green lachrymatory liquid (11.5 g) containing 2-(bromomethyl)benzoyl cyanide O-methyloxime.

A solution of part of the crude 2-(bromomethyl)benzoyl cyanide O-methyloxime (3.6 g) in DMF was added dropwise to a stirred solution of sodium 2-methylphenoxide [prepared from 2-methylphenol (1.75 g) and sodium hydride (0.34 g)] in DMF (total volume of DMF=30 ml) and the resulting mixture was stirred for 10 minutes before being diluted with water and extracted with ethyl acetate. The extracts were dried and concentrated to give a viscous brown oil (3.5 g) which crystallised on standing. Analysis of this crude product by GC, and comparison with GC traces from the purified materials described below, showed that the crude product contained a roughly 10:1 mixture of stereoisomers of 2-(2-methylphenoxymethyl)benzoyl cyanide O-methyloxime. Purification of the crude product by chromatography using mixtures of hexane and ether as eluant, and trituration of the appropriate fractions with hexane, gave a single stereoisomer (isomer 1, the major isomer) of 2-(2-methylphenoxymethyl)benzoyl cyanide O-methyloxime (1.2 g, 27% yield from 2-methylbenzoyl cyanide O-methyloxime) as a white solid, mp 53°–4° C., $^1$H NMR (CDCl$_3$): δ 2.3 (3H,s), 4.1 (3H,s), 5.3 (2H,s), 6.8 (1H,d), 6.9 (1H,t), 7.15 (2H,m), 7.5 (2H,m), 7.75 (2H,d) ppm. A small sample of the minor stereoisomer (isomer 2) of 2-(2-methylphenoxymethyl)-benzoyl cyanide O-methyloxime was obtained from the mother liquors of the trituration described above using chromatography with ethyl acetate:hexane (5:95) as eluant; it was a yellow oil, $^1$H NMR (CDCl$_3$): δ 2.3 (3H,s), 4.05 (3H,s), 5.05 (2H,s), 6.8 (1H,d), 6.9 (1H,t), 7.15 (2H,t), 7.4 (2H,t), 7.5 (1H,t), 7.65 (1H,d) ppm.

A mixture of part of the sample of isomer 1 of 2-(2-methylphenoxymethyl) benzoyl cyanide O-methyloxime (280 mg), hydroxylamine hydrochloride (80 mg) and triethylamine (110 mg) in methanol (5 ml) was heated under reflux for 5 hours. The reaction mixture was concentrated and the residue, dissolved in ethyl acetate, was washed with water, dried, concentrated, and chromatographed using ethyl acetate:hexane (1:1) as eluant to give two stereoisomers of 2-[2-(2-methylphenoxymethyl)phenyl]-2-methoxyimino acetamide oxime. Isomer I (200 mg, 67% yield), eluted first, was a white solid, mp 140° C., $^1$H NMR (CDCl$_3$): δ 2.3 (3H,s), 4.0 (3H,s) and 5.05 (2H,s) ppm. Isomer II (100 mg, 33% yield), was also a white solid, mp 110°–2° C., $^1$H NMR (CDCl$_3$): δ 2.3 (3H,s), 4.0 (3H,s) and 5.2 (2H,s) ppm.

A mixture of part of the sample of isomer I of 2-[2-(2-methylphenoxymethyl)phenyl]-2-methoxyimino acetamide oxime (150 mg), trimethyl orthoformate (3 ml) and concentrated sulphuric acid (3 drops) was heated under reflux for 2 hours, then allowed to cool, concentrated and chromatographed using ether:hexane (30:70) as eluant to give isomer A of the title compound (100 mg, 62% yield) as a viscous oil which crystallised on standing, mp 65°–6° C., $^1$H NMR (CDCl$_3$): δ 2.3 (3H,s), 4.1 (3H,s), 5.2 (2H,s), 6.75 (1H,d), 6.85 (1H,t), 7.15 (2H,m), 7.4 (2H,m), 7.5 (1H,t), 7.7 (1H,d), 8.8 (1H,s) ppm. Under the same reaction conditions, isomer II of 2-[2-(2-methylphenoxymethyl)phenyl]-2-methoxyimino acetamide oxime was also converted into isomer A of the title compound, though the transformation was significantly slower than the conversion of isomer I into isomer A of the title compound. The geometric isomer (isomer B) of the title compound was obtained by irradiating a solution of isomer A of the title compound (10 mg) in methanol (3 ml) with 360 nm light for about 12 hours and then chromatographing the resulting mixture of geometric isomers using hexane:ethyl acetate (4:1) as eluant. It was obtained as an oil (2 mg), $^1$H NMR (CDCl$_3$): δ 2.2(3H,s), 4.1(3H,s), 5.0(2H,s), 6.75(1H,d), 6.85(1H,t), 7.10(2H,m), 7.3(1H,d), 7.5(2H,m), 7.7(1H,d) and 8.8(1H,s) ppm.

EXAMPLE 6

This Example illustrates the preparation of (E)-2-[2-(6-trifluoromethylpyrid-2-yloxymethyl)benzoyl]oxa-1,3,4-diazole O-methyloxime (Compound No. 92 of Table 4).

(E)-2-(2-Methylbenzoyl)oxa-1,3,4-diazole O-methyloxime (3.60 g), N-bromosuccinimide (NBS) (3.40 g) and azo-bis(iso-butyronitrile) (AIBN) (trace) were mixed and stirred in carbon tetrachloride (CCl$_4$) (100 ml) at reflux, while being illuminated with a 300 watt lamp. After 3 hours the reaction was cooled and filtered and the CCl$_4$ evaporated to yield an oil containing approximately 80% of (E)-2-[(2-bromomethyl)benzoyl]oxa-1,3,4-diazole) O-methyloxime as a brown/green oil (5.5 g). $^1$H NMR (CDCl$_3$):δ 4.15(3H,s); 4.40(2H,s); 7.30–7.60(4H.m); 8.50(1H,s) ppm.

The compound was used without further purification.

The bromomethyl oxadiazole (0.285 g), 6-trifluoromethyl-2-pyridone (0.161 g) and potassium carbonate (0.138 g) were stirred at room temperature in dry DMF (3 ml) for 2 hours, and then stood overnight. The mixture was poured into water and extracted with diethyl ether. The ethereal solution was washed with water and then dried over magnesium sulphate, and evaporated to yield an oil (0.35 g). The oil was purified by column chromatography on silica gel, eluting with hexane:diethyl ether (1:2) to give the title compound as an oil (0.110 g). $^1$H NMR (CDCl$_3$): δ 4.1(s,3H); 5.45(s,2H); 6.65(d,1H); 6.9–7.0(2d,1H); 7.2(d,1H); 7.35(dd,1H); 7.5(m,2H); 7.65(t,2H); 8.45(s,1H) ppm.

EXAMPLE 7

This Example illustrates the preparation of (E)-3-[2-(6-trifluoromethylpyrid-2-yloxymethyl)benzoyl]oxa-1,2,4-diazole O-methyloxime (Compound No. 92 of Table 6).

(E)-3-(2-Methylbenzoyl)oxa-1,2,4-diazole O-methyloxime (6.0 g), N-bromosuccinimide (NBS) (5.3 g) and dibenzoyl peroxide (trace) were mixed and stirred in CCl$_4$ (150 ml) at reflux, while being illuminated with a 300 watt lamp. After 2 hours the reaction was filtered through celite, further NBS (2.5 g) and dibenzoyl peroxide (trace) were added and the reaction refluxed for a further 2 hours. Then azo-bis(iso-butyronitrile) (trace) was added and the reaction refluxed for another 2 hours. The reaction mixture was filtered and evaporated to give a brown oil (8.2 g). This was purified twice by column chromatography on silica gel, eluting with hexane:diethyl ether (1:1) to give an oil, containing approximately 70% of (E)-3-[(2-bromomethyl)-benzoyl]oxa-1,2,4-diazole O-methyloxime as an oil. $^1$H NMR (CDCl$_3$): δ 4.13(s,3H); 4.40(s,2H); 7.15-7.6(m,4H); 8.8(s,1H) ppm.

The bromomethyl oxadiazole (0.140 g), 6-trifloromethyl-2-pyridone (0.08 g) and potassium carbonate (0.07 g) in dry DMF (3 ml) were stirred for 2 hours, and then stirred overnight. The reaction was poured into water and extracted with diethyl ether. The ethereal solution was washed with water, dried over magnesium sulphate and evaporated to give a crude product. The crude product was purified by column chromatography on silica gel, eluting with hexane:diethyl ether (1:2), to give the title compound as an oil (0.105 g).

$^1$H NMR (CDCl$_3$): δ 4.1(s,3H), 5.4(s,2H), 6.7(d,1H), 7.2(d,1H), 7.3(dd,1H), 7.5(m,2H), 7.65(t,2H); 8.75(s,1H) ppm.

EXAMPLE 8

The compounds were tested against a variety of foliar fungal diseases of plants. The technique employed was as follows.

The plants were grown in John Innes Potting Compost (No 1 or 2) in 4 cm diameter minipots. The test compounds were formulated either by bead milling with aqueous DISPERSOL T or as a solution in acetone or acetone/ethanol which was diluted to the required concentration immediately before use. The formulations (100 ppm active ingredient) were sprayed on to the foliage or applied to the roots of the plants in the soil. The sprays were applied to maximum retention and the root drenches to a final concentration equivalent to approximately 40 ppm a.i. in dry soil. TWEEN 20 was added to give a final concentration of 0.05% when the sprays were applied to cereals.

For most of the tests the compounds were applied to the soil (roots) or to the foliage (by spraying) one or two days before the plant was inoculated with the disease. Exceptions were the test on *Erysiphe graminis* in which the plants were inoculated 24 hours before treatment and the test on *Puccinia recondita* in which the plants were inoculated 48 hours before treatment. Foliar pathogens were applied by spray as zoosporangial suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease level present (i.e. leaf area covered by actively sporulating disease) on each of the treated plants was recorded using the following assessment scale:

| | |
|---|---|
| 0 = 0% disease present | 20 and 24 = 10.1–20% disease present |
| 1 = 0.1–1% disease present | 30 = 20.1–30% disease present |
| 3 = 1.1–3% disease present | 60 = 30.1–60% disease present |
| 5 = 3.1–5% disease present | 90 and 94 = 60.1–100% disease present |
| 10 = 5.1–10% disease present | |

Each assessment was then expressed as a percentage of the level of disease present on the untreated control plants. This calculated value is referred to as a POCO (Percentage of Control) value. An example of a typical calculation is as follows:

Disease level on untreated control=90

Disese level on treated plant=30

$$POCO = \frac{\text{disease level on treated plant}}{\text{disease level on untreated control}} \times 100 = \frac{30}{90} \times 100 = 33.3$$

This calculated POCO value is then rounded to the nearest of the values in the 9-point assessment scale shown above. In this particular example, the POCO value would be rounded to 30. If the calculated POCO falls exactly mid-way between two of the points, it is rounded to the lower of the two values.

The results displayed in Table II below represent these rounded POCO values.

TABLE II

| Compound No (Table No) | Pr | Egt | Sn | Po | Tc | Vi | Pv | Pil |
|---|---|---|---|---|---|---|---|---|
| 2(1) | 90a | 30a | 90a | 30a | 90a | 5a | 90a | 90a |
| 2(2)* | 90a | 30a | 90a | 20a | 90a | 90a | 90a | 90a |
| 2(3) | 90 | 5 | 30 | 0 | — | — | 0 | 90 |
| 1(4) | — | 60 | — | 60 | 90 | 0 | 0 | 30 |
| 2(4)* | — | 90b | 90b | 0b | — | — | 90b | — |
| 2(4)** | — | 90b | 90b | 0b | — | — | 90b | — |
| 35(4) | 90 | 0 | 0 | 10 | 90 | 0 | 0 | 90 |
| 62(4) | 0b | 0b | 10b | — | 5b | 0b | 10b | 30b |
| 92(4) | 90 | 10 | 0 | — | 90 | 0 | 0 | 90 |
| 99(4) | 0b | 10b | 0b | 20b | 90b | 30b | 90b | 90b |
| 35(6)* | 90 | 90 | 90 | — | — | 90 | 60 | 90 |
| 62(6) | 90 | 30 | 90 | — | — | 90 | 90 | 30 |
| 92(6) | 90 | 90 | 30 | — | 90 | 90 | 20 | 90 |
| 35(8) | 90b | 90b | 90b | — | 90b | 0b | 90b | 90b | a = 10 ppm foliar application only
b = 25 ppm foliar application only
— = No result
* = Stereoisomer A
** = Mixture of stereoisomers B:A
Key to diseases
Pr *Puccinia recondita*
Egt *Erysiphe graminis tritici*
Sn *Septoria nodorum*
Po *Pyricularia oryzae*
Tc *Thanetophorus cucumeris*
Vi *Venturia inaequalis*
Pv *Plasmopara viticola*
Pil *Phytophthora infestans lycopersici*

CHEMICAL FORMULAE
(IN DESCRIPTION)

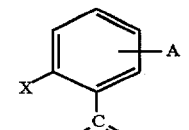

(I)

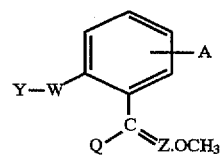

(Ie)

-continued
CHEMICAL FORMULAE
(IN DESCRIPTION)
(If)
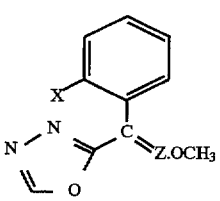
(Ig)
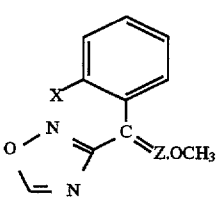
(Ih)
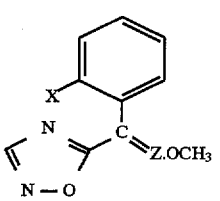
(Ii)
Scheme 1
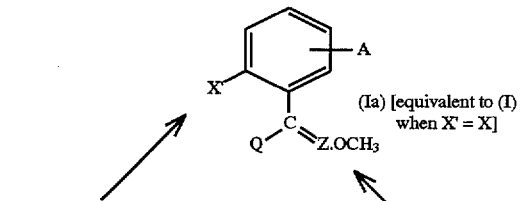
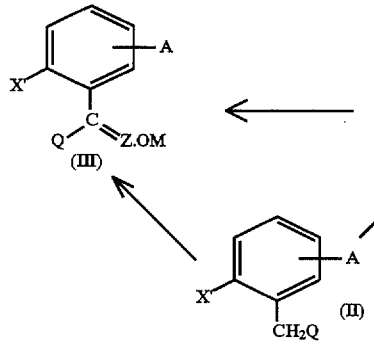
Scheme 2
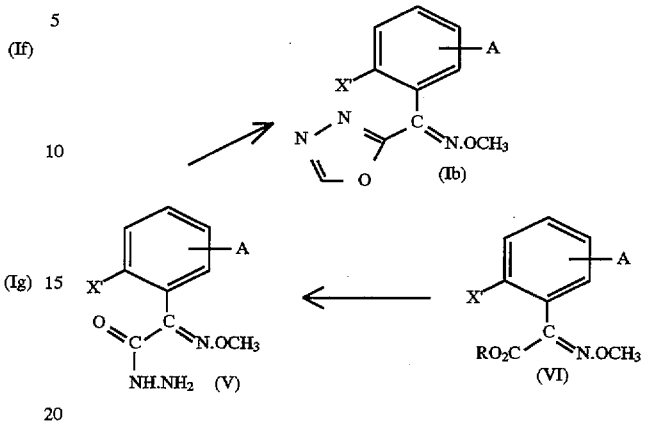
Scheme 3
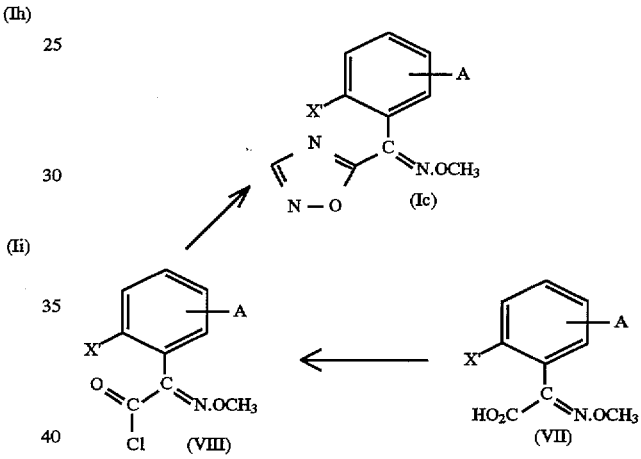
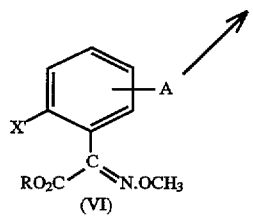

Scheme 4

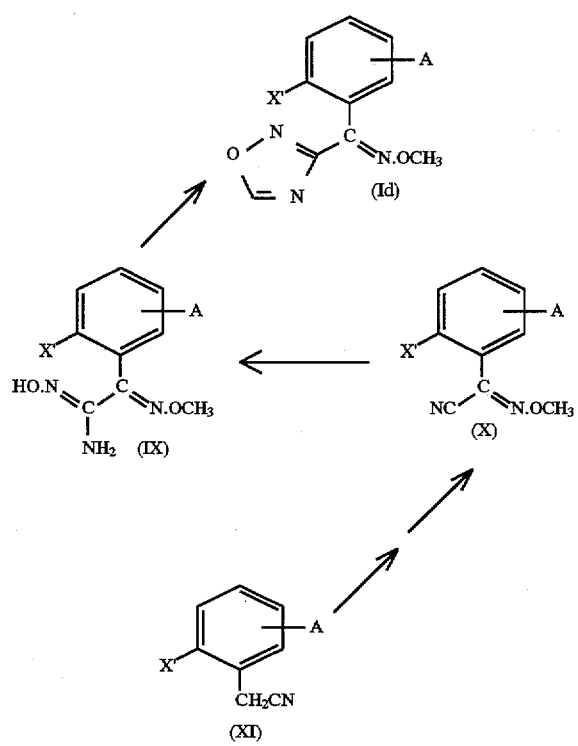

Scheme 5

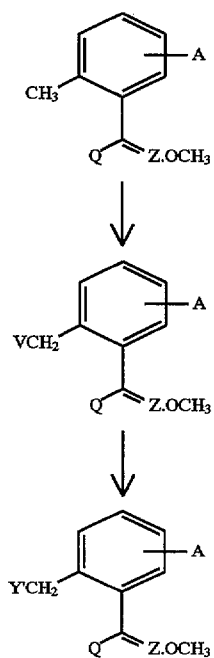

Scheme 6

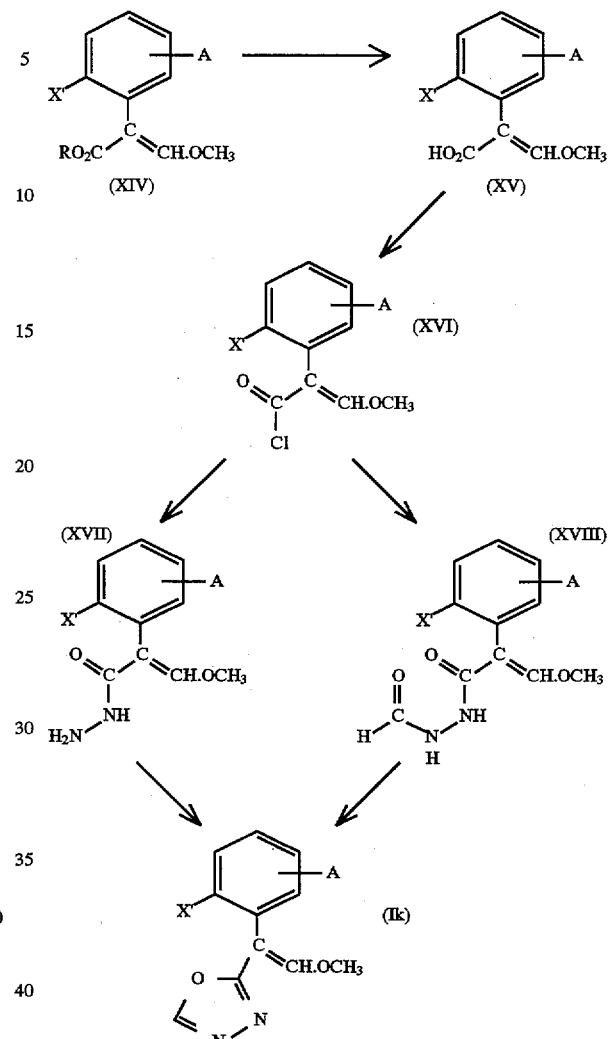

We claim:
1. A compound of formula (I):

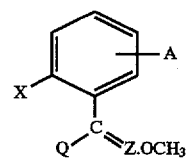

wherein Q is oxazol-2-yl, 1,3,4-oxadiazol-2-yl, 1,2,4-oxadiazol-3-yl or 1,2,4-oxadiazol-5-yl; Z is CH or N; A is hydrogen, halogen, $C_{1-4}$ alkyl, $C_{1-4}$ alkoxy, cyano, nitro or trifluoromethyl; X is halogen, $C_{1-8}$ alkyl, $C_{1-8}$ haloalkyl, $C_{1-8}$ hydroxyalkyl, $C_{1-8}$ alkoxy($C_{1-8}$)alkyl, $C_{1-8}$ haloalkoxy ($C_{1-8}$)alkyl, aryl($C_{1-8}$)alkyl, aryloxy($C_{1-8}$)alkyl, heteroaryl ($C_{1-8}$) alkyl, heteroaryloxy($C_{1-8}$) alkyl, $C_{3-6}$ cycloalkyl($C_{1-8}$)alkyl, arylthio($C_{1-8}$)alkyl, heteroarylthio ($C_{1-8}$)alkyl, $R^1R^{2'}C=NO(C_{1-8})$alkyl, $C_{2-8}$ alkenyl, $C_{2-8}$ alkynyl, $C_{2-8}$ haloalkenyl, $C_{2-8}$ haloalkynyl, aryl($C_{2-8}$)

alkenyl, aryl($C_{2-8}$)alkynyl, aryloxy($C_{2-8}$)alkenyl, aryloxy ($C_{2-8}$) alkynyl, arylthio($C_{2-8}$)alkenyl, arylthio($C_{1-8}$)alkynyl, heteroaryl($C_{2-8}$)alkenyl, heteroaryl($C_{2-8}$)alkynyl, heteroaryloxy($C_{2-8}$)alkenyl, heteroaryloxy($C_{2-8}$)alkynyl, heteroarylthio($C_{2-8}$)alkenyl, heteroarylthio($C_{2-8}$)alkynyl, aryl, heteroaryl, $C_{3-6}$ cycloalkyl, $OR^1$, $SR^1$, $SOR^1$, $SO_2R^1$, $COR^1$, $CO_2R^1$, $NR^1R^2$ or $CONR^1R^2$; and $R^1$ and $R^2$ are, independently, hydrogen, $C_{1-8}$ alkyl, $C_{1-8}$ haloalkyl, $C_{1-8}$ hydroxyalkyl, $C_{1-8}$ alkoxy($C_{1-8}$)alkyl, $C_{1-8}$ haloalkoxy($C_{1-8}$)alkyl, aryl($C_{1-8}$)alkyl, aryloxy($C_{1-8}$) alkyl, heteroaryl($C_{1-8}$) alkyl, heteroaryloxy($C_{1-8}$) alkyl, $C_{3-6}$ cycloalkyl($C_{1-8}$)alkyl, arylthio($C_{1-8}$)alkyl, heteroarylthio ($C_{1-8}$)alkyl, $C_{2-8}$ alkenyl, $C_{2-8}$alkynyl, $C_{2-8}$ haloalkenyl, $C_{2-8}$ haloalkynyl, aryl($C_{2-8}$)alkenyl, aryl($C_{2-8}$)alkynyl, aryloxy ($C_{2-8}$) alkenyl, aryloxy($C_{2-8}$)alkynyl, arylthio($C_{1-8}$)alkenyl, arylthio($C_{1-8}$)alkynyl, heteroaryl($C_{2-8}$)alkenyl, heteroaryl ($C_{2-8}$)alkynyl, heteroaryloxy($C_{2-8}$)alkenyl, heteroaryloxy ($C_{2-8}$)allynyl, heteroarylthio($C_{2-8}$)alkenyl, heteroarylthio ($C_{2-8}$)alkynyl, aryl, heteroaryl, or $C_{3-6}$ cyclolkyl; $R^{1'}$ and $R^{2'}$ are, independently, hydrogen, $C_{1-8}$ alkyl, $C_{1-8}$ haloalkyl, $C_{1-8}$ hydroxyalkyl, $C_{1-8}$ alkoxy($C_{1-8}$)alkyl, $C_{1-8}$ haloalkoxy ($C_{1-8}$) alkyl, aryl($C_{1-8}$)alkyl, aryloxy($C_{1-8}$)alkyl, heteroaryl ($C_{1-8}$) alkyl, heteroaryloxy($C_{1-8}$) alkyl, $C_{3-6}$ cycloalkyl($C_{1-8}$)alkyl, arylthio($C_{1-8}$)alkyl, heteroarylthio ($C_{1-8}$)alkyl, $C_{2-8}$) alkenyl, $C_{2-8}$ alkynyl, $C_{2-8}$ haloalkenyl, $C_{2-8}$ haloalkynyl, aryl($C_{2-8}$)alkenyl, aryl($C_{2-8}$)alkynyl, aryloxy($C_{2-8}$)alkenyl, aryloxy($C_{2-8}$)alkynyl, arylthio($C_{2-8}$) alkenyl, arylthio($C_{1-8}$)alkynyl, heteroaryl($C_{2-8}$)alkenyl, heteroaryl($C_{2-8}$)alkynyl, heteroaryloxy($C_{2-8}$)alkenyl, heteroaryloxy($C_{2-8}$)alkynyl, heteroarylthio($C_{2-8}$)alkenyl, heteroarylthio($C_{2-8}$)alkynyl, aryl, heteroaryl, $C_{3-6}$ cycloalkyl, $C_{1-8}$ alkoxy, $C_{1-8}$ haloalkoxy, aryloxy, heteroaryloxy, nitro, halogen, NR'R" or cyano, or $R^{1'}$ and $R^{2'}$ join to form either a $C_{5-10}$ aliphatic, aromatic or mixed aliphatic/aromatic carbocyclic ring system or a 5- to 10-membered heterocyclic ring system; the foregoing aryl and heteroaryl rings are optionally substituted with:halogen, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$) alkyl, halo($C_{1-4}$)alkoxy, $C_{1-4}$ alkylthio, hydroxy($C_{1-4}$)alkyl, $C_{1-4}$ alkoxy($C_{1-4}$)alkyl, $C_{3-6}$ cycloalkyl, $C_{3-6}$ cycloalkyl($C_{1-4}$)alkyl, methylenedioxy optionally substituted with fluorine or $C_{1-4}$ alkyl, aryl, heteroaryl, heterocyclyl, aryloxy, heteroaryloxy, aryl($C_{1-4}$)alkyl wherein the alkyl moiety is optionally substituted with hydroxy, heteroaryl($C_{1-4}$)alkyl, aryl($C_{2-4}$) alkenyl, heteroaryl($C_{2-4}$)alkenyl, aryl($C_{1-4}$)alkoxy, heteroaryl($C_{1-4}$) alkoxy, aryloxy($C_{1-4}$)alkyl, heteroaryloxy($C_{1-4}$)alkyl, $C_{1-4}$ alkanoyloxy, benzoyloxy, cyano, thiocyanato, nitro, —NR'R", —NHCOR', —NHCONR'R", —CONR'R", —COOR', —OSO$_2$R', —SO$_2$R', —COR', —CR'=NR" or —N=CR'R", or two substituents, when they are in adjacent positions on the aryl or heteroaryl ring can join to form a fused aliphatic ring; substituents which may be present in the aryl or heteroaryl rings of any of the foregoing substituents include one or more of the following:halo, hydroxy, mercapto, $C_{1-4}$alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$)alkyl, halo($C_{1-4}$)alkoxy, $C_{1-4}$ alkylthio, hydroxy($C_{1-4}$)alkyl, $C_{1-4}$ alkoxy($C_{1-4}$)alkyl, $C_{3-6}$ cycloalkyl, $C_{3-6}$ cycloalkyl($C_{1-4}$) alkyl, alkanoyloxy, benzoyloxy, cyano, thiocyanato, nitro, —NR'R", —NHCOR'. —NHCONR'R", —CONR'R", —COOR', —OSO$_2$R', —SO$_2$R', —COR', —CR'=NR" or —N=CR'R"; R' and R" are independently hydrogen, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy; when R' and R" are in CONR'R" they can together form a 5- or 6-membered heterocyclic ring; aryl is phenyl or napthyl; heteroaryl is pyridinyl, pyrimidinyl, pyridazinyl, pyrazinyl, 1,2,3-, 1,2,4- or 1,3,5-triazinyl, furyl, thienyl, pyrrolyl, pyrazolyl, imidazolyl, 1,2, 3- or 1,2,4-triazolyl, oxazolyl, isoxazolyl, thiazolyl, isothiazolyl, quinolinyl, isoquinolinyl, cinnolinyl, quinazolinyl, quinoxalinyl, indolinyl, isoindolinyl, 1- or 2-benzofuranyl, 1- or 2-benzothienyl, benzimidazolinyl, 1,2, 4-oxadiazolyl, 1,3,4-oxadiazolyl, 1,2,4-thiadiazolyl, 1,3,4-thiadiazolyl, benzisoxazolyl, benzisothiazolyl, benzpyrazolyl, benzoxazolyl, benzthiazolyl, tetrazolyl and thiazolo[5,4-b]pyrid-2-yl, or an N-oxide thereof.

2. A compound as claimed in claim 1 wherein X is $R^{1"}R^{2'}C=NOCH_2$; $R^{1'}$ is aryl, heteroaryl, aryloxy, heteroaryloxy, aryl($C_{1-8}$)alkyl, heteroaryl($C_{1-8}$)alkyl, aryloxy($C_{1-8}$) alkyl or heteroaryloxy($C_{1-8}$)alkyl; the foregoing aryl and heteroaryl rings are defined as in claim 1; $R^{2'}$is methyl, cyano, hydrogen, chlorine or amino; and Q, Z and A are as defined in claim 1.

3. A compound as claimed in claim 1 wherein X is aryloxymethyl, heteroaryloxymethyl or heteroaryloxy; and the foregoing aryl and heteroaryl rings are optionally substituted as defined as in claim 1.

4. A compound as claimed in claim 1, wherein Q is 1,3,4-oxadiazol-2-yl.

5. A compound of formula (I) as claimed in claim 1, wherein Z is N or CH; Q is 1,3,4-oxadiazol-2-yl; and A is hydrogen.

6. The intermediate of formula (I):

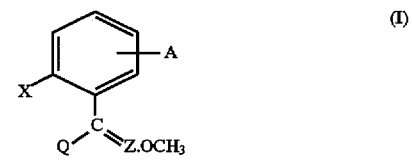

(I)

wherein A is hydrogen, Q is oxaol-2-yl, 1,3,4-oxadiazol-2-yl, 1,2,4-oxadiazol-3-yl or 1,2,4-oxadiazol-5-yl, Z is CH or N; and X is chloromethyl, bromomethyl or iodomethyl.

7. A fungicidal composition comprising a fungicidally effective amount of a compound according to claim 1 and a fungicidally acceptable carrier or diluent therefor.

8. A method of combating fungi which comprises applying to plants, to the seeds of plants or to the locus of the plants or seeds, a compound according to claim 1.

9. A method of combating fungi which comprises applying to plants, to the seeds of plants or to the locus of the plants or seeds, a composition according to claim 7.

* * * * *